US012742165B2

(12) United States Patent
Hucklenbroich et al.

(10) Patent No.: US 12,742,165 B2
(45) Date of Patent: Sep. 22, 2026

(54) ISOLATION OF NUCLEIC ACIDS AT ELEVATED TEMPERATURES

(71) Applicant: Bioecho Life Sciences GMBH, Cologne (DE)

(72) Inventors: Joerg Hucklenbroich, Wermelskirchen (DE); Maximilian Weiter, Cologne (DE); Markus Helmut Mueller, Dormagen (DE); Nicole Seip, Kaarst (DE); Benedikt Buerfent, Bergheim (DE)

(73) Assignee: Bioecho Life Sciences GMBH, Cologne (DE)

( * ) Notice: Subject to any disclaimer, the term of this patent is extended or adjusted under 35 U.S.C. 154(b) by 686 days.

(21) Appl. No.: 17/620,465

(22) PCT Filed: May 14, 2021

(86) PCT No.: PCT/EP2021/062856
§ 371 (c)(1),
(2) Date: Dec. 17, 2021

(87) PCT Pub. No.: WO2021/229066
PCT Pub. Date: Nov. 18, 2021

(65) Prior Publication Data

US 2023/0303995 A1 Sep. 28, 2023

(30) Foreign Application Priority Data

May 14, 2020 (EP) .................................... 20174548
May 14, 2020 (EP) .................................... 20174550
May 14, 2020 (LU) .................................. LU101791

(51) Int. Cl.
*C12N 15/10* (2006.01)
*C12Q 1/686* (2018.01)
*C12Q 1/6869* (2018.01)

(52) U.S. Cl.
CPC ......... *C12N 15/1003* (2013.01); *C12Q 1/686* (2013.01); *C12Q 1/6869* (2013.01)

(58) Field of Classification Search
None
See application file for complete search history.

(56) References Cited

U.S. PATENT DOCUMENTS

2009/0131650 A1* 5/2009 Brahmasandra ......... C07H 1/08 536/25.4
2009/0227011 A1* 9/2009 Chen .................. C12N 15/1003 435/320.1
2009/0312285 A1* 12/2009 Fischer ................ C12Q 1/6806 435/5
2014/0038174 A1* 2/2014 Fischer .................. C12Q 1/701 435/6.12
2016/0289735 A1* 10/2016 Gerdes ................. C12Q 1/6804
2020/0056169 A1* 2/2020 Müller ............... C12N 15/1017

FOREIGN PATENT DOCUMENTS

WO 2006138444 A2 12/2006
WO 2009085355 A2 7/2009
WO WO-2010136503 A1 * 12/2010 ......... C12N 15/1003
WO 2011034864 A1 3/2011
WO 2013148346 A1 10/2013
WO 2013165870 A1 11/2013
WO 2016109799 A2 7/2016

OTHER PUBLICATIONS

Capto Core 700, Sigma-Aldrich, retrieved from https://www.sigmaaldrich.com/US/en/product/sigma/ (Year: 2026).*
Burden (2008) "Guide to the Homogenization of Biological Samples" Random Primers, Issue No. 7, Sep. 2008, p. 1-14.
Haotian Wu et al., "Rapid method for the isolation of mammalian sperm DNA", Biotechniques Informa Healthcare, US, vol. 58, Nr: 6, pp. 293-300.
International Search Report and Written Opinion for App. No. PCT/EP2021/062856, dated Oct. 18, 2021, 9 pages.

* cited by examiner

*Primary Examiner* — Dale R Miller
(74) *Attorney, Agent, or Firm* — Riverside Law LLP

(57) ABSTRACT

The present invention relates to a method and use for isolating nucleic acids from a sample using a solution comprising a reducing agent, preferably a reducing agent of formula (I), an anionic detergent and a buffering substance. The present invention also relates to solutions comprising a reducing agent, preferably a reducing agent of formula (I), an anionic detergent and a buffering substance; as well as a kit comprising said solutions.

17 Claims, 21 Drawing Sheets

| # | Type of sample | Protocol | Nucleic acid (ng/uL) | A260/A280 | A260/A230 | A260 | A280 |
|---|---|---|---|---|---|---|---|
| **4** | 30 mg muscle tissue | TCEP – Lysis with Beadbeating | 47.301 | 1.674 | 0.601 | 0.946 | 0.565 |
| **5** | 30 mg muscle tissue | TCEP – Lysis with Beadbeating | 84.595 | 1.918 | 0.475 | 1.692 | 0.882 |
| **6** | 30 mg muscle tissue | TCEP – Lysis with Beadbeating | 44.305 | 1.816 | 0.669 | 0.886 | 0.488 |

Fig. 8

| # | bacterium | Reducing agent (20mM) | Nucleic acid (ng/uL) | A260/A280 | A260/A230 | A260 corrected | A280 | Total amount of obtained nucleic acid in µg | % nucleic acid in µg from total TCEP (= 100 %) |
|---|---|---|---|---|---|---|---|---|---|
| 1 | P.fluorescence | N-acetylcysteamine | 247.811 | 2.063 | 2.386 | 4.956 | 2.403 | 259.92 | 36.71 % |
| 2 | P.fluorescence | N-acetylcysteamine | 272.031 | 2.064 | 2.356 | 5.441 | 2.635 | | |
| 3 | P.fluorescence | Na-thiosulfat 5 hydrate | 94.229 | 2.01 | 2.262 | 1.885 | 0.938 | 151.59 | 21.41 % |
| 4 | P.fluorescence | Na-thiosulfat 5 hydrate | 208.943 | 2.059 | 2.384 | 4.179 | 2.029 | | |
| 5 | P.fluorescence | Na-hydrosulfite | 442.452 | 2.081 | 2.328 | 8.849 | 4.253 | 438.40 | 61.93 % |
| 6 | P.fluorescence | Na-hydrosulfite | 434.34 | 2.068 | 2.313 | 8.687 | 4.201 | | |
| 7 | P.fluorescence | L-Gluthathione red. | 507.214 | 2.083 | 2.323 | 10.144 | 4.869 | 446.95 | 63.14 % |
| 8 | P.fluorescence | L-Gluthathione red. | 386.681 | 2.079 | 2.37 | 7.734 | 3.72 | | |
| 9 | P.fluorescence | 1-Propanethiol | 102.854 | 2.021 | 2.321 | 2.057 | 1.018 | 132.15 | 18.66 % |
| 10 | P.fluorescence | 1-Propanethiol | 161.447 | 2.059 | 2.383 | 3.229 | 1.568 | | |
| 11 | P.fluorescence | TCEP | 561.373 | 1.96 | 2.241 | 11.227 | 5.729 | 707.86 | 100 % |
| 12 | P.fluorescence | TCEP | 854.354 | 1.936 | 2.257 | 17.087 | 8.827 | | |

Fig. 9

| # | bacterium | Reducing agent (20mM) | Nucleic acid (ng/uL) | A260/ A280 | A260/ A230 | A260 corrected | A280 | Total amount of obtained nucleic acid in µg | % nucleic acid in µg from total TCEP (= 100 %) |
|---|---|---|---|---|---|---|---|---|---|
| 1 | P.fluorescence | Ammonium thioglycolate | 52.123 | 1.995 | 2.134 | 1.042 | 0.522 | 54.05 | 22.02 % |
| 2 | P.fluorescence | Ammoniumthioglycolate | 55.985 | 1.866 | 1.942 | 1.12 | 0.6 | | |
| 3 | P.fluorescence | L-Cystein hydrochloride | 75.21 | 1.899 | 2103 | 1.504 | 0.792 | 81.15 | 33.07 % |
| 4 | P.fluorescence | L-Cystein hydrochloride | 87.088 | 1.875 | 1.779 | 1.742 | 0.929 | | |
| 5 | P.fluorescence | Sodium thioglycolate | 40.92 | 1.942 | 1.981 | 0.818 | 0.421 | 43.34 | 17.66 % |
| 6 | P.fluorescence | Sodium thioglycolate | 45.762 | 1.85 | 1.892 | 0.915 | 0.495 | | |
| 7 | P.fluorescence | DTT | 40.366 | 1.838 | 1.873 | 0.807 | 0.439 | 44.00 | 17.93 % |
| 8 | P.fluorescence | DTT | 47.634 | 1.954 | 1.973 | 0.953 | 0.488 | | |
| 9 | P.fluorescence | TCEP | 239.789 | 1.897 | 2.179 | 4.796 | 2.529 | 245.36 | 100 % |
| 10 | P.fluorescence | TCEP | 250.931 | 1.905 | 1.995 | 5.019 | 2.635 | | |

Fig. 10

| # | bacterium | Reducing agent (20mM) | Nucleic acid sequences (ng/uL) | A260/ A280 | A260/ A230 | A260 corrected | A280 | Total amount of obtained nucleic acid in µg | % nucleic acid in µg from total TCEP (= 100 %) | Time at 80°C in min |
|---|---|---|---|---|---|---|---|---|---|---|
| 1 | P.fluorescence | N-acetylcysteamine | 197.331 | 2.005 | 2.255 | 3.947 | 1.968 | 214.99 | 24.00 % | 10 |
| 2 | P.fluorescence | N-acetylcysteamine | 232.64 | 2.016 | 2.232 | 4.653 | 2.308 | | | 10 |
| 3 | P.fluorescence | Sodium thiosulfate | 167.892 | 2.032 | 2.331 | 3.358 | 1.652 | 194.39 | 21.70 % | 10 |
| 4 | P.fluorescence | Sodium thiosulfate | 220.896 | 2.041 | 2.269 | 4.418 | 2.165 | | | 10 |
| 5 | P.fluorescence | Sodium hydrosulfite | 464 | 2.066 | 2.333 | 9.28 | 4.492 | 484.94 | 54.14 % | 10 |
| 6 | P.fluorescence | Sodium hydrosulfite | 505.883 | 2.045 | 2.195 | 10.118 | 4.947 | | | 10 |
| 7 | P.fluorescence | L-Gluthathione red. | 471.974 | 2.027 | 2.316 | 9.439 | 4.657 | 506.71 | 56.57 % | 10 |
| 8 | P.fluorescence | L-Gluthathione red. | 541.455 | 2.025 | 2.328 | 10.829 | 5.348 | | | 10 |
| 9 | P.fluorescence | Ammonium thioglycolate | 357.965 | 2.043 | 2.351 | 7.159 | 3.504 | 396.28 | 44.24 % | 10 |
| 10 | P.fluorescence | Ammonium thioglycolate | 434.589 | 2.065 | 2.34 | 8.692 | 4.21 | | | 10 |
| 11 | P.fluorescence | L-Cystein hydrochloride | 496.97 | 2.063 | 2.349 | 9.939 | 4.817 | 535.94 | 59.84 % | 10 |
| 12 | P.fluorescence | L-Cystein hydrochloride | 574.905 | 2.048 | 2.273 | 11.498 | 5.615 | | | 10 |
| 13 | P.fluorescence | TCEP | 893.629 | 2.004 | 2.243 | 17.873 | 8.916 | 895.60 | 100 % | 5 |
| 14 | P.fluorescence | TCEP | 897.574 | 2.001 | 2.235 | 17.951 | 8.972 | | | 5 |
| 15 | P.fluorescence | Sodium sulfite | 242.618 | 2.018 | 2.17 | 4.852 | 2.404 | 254.93 | 28.46 % | 10 |
| 16 | P.fluorescence | Sodium sulfite | 267.245 | 2.016 | 2.053 | 5.345 | 2.651 | | | 10 |
| 17 | P.fluorescence | No reducing agent | 197.07 | 2.03 | 2.33 | 3.94 | 1.94 | 198.83 | 22.20 % | 10 |
| 18 | P.fluorescence | No reducing agent | 200.59 | 2.01 | 2.34 | 4.01 | 1.99 | | | 10 |

Fig. 11

| # | bacterium | Reducing agent + different buffer (20mM) | Nucleic acids(ng/uL) | A260/ A280 | A260/ A230 | A260 corrected | A280 | Total amount of obtained nucleic acid in µg | Time at 80°C in min |
|---|---|---|---|---|---|---|---|---|---|
| 1 | P.fluorescence | TCEP in TE-BE pH 7.0 | 606.705 | 2.031 | 2.046 | 12.134 | 5.974 | 605.33 | 5 |
| 2 | P.fluorescence | TCEP in TE-BE pH7.0 | 603.946 | 2.046 | 2.05 | 12.079 | 5.903 | | 5 |
| 3 | P.fluorescence | TCEP in Cell Buffer | 954.832 | 1.976 | 2.174 | 19.097 | 9.662 | 955.73 | 5 |
| 4 | P.fluorescence | TCEP in Cell Buffer | 956.627 | 1.993 | 2.219 | 19.133 | 9.599 | | 5 |
| 5 | P.fluorescence | Cell Buffer | 286.389 | 2.076 | 2.352 | 5.728 | 2.76 | 289.49 | 5 |
| 6 | P.fluorescence | Cell Buffer | 292.597 | 2.095 | 2.363 | 5.852 | 2.793 | | 5 |

Fig. 12

| # | Temp. in °C | pH | TCEP in mM | Time of lysis | Obtained amount of nucleic acids [ng/µL] | Yield compared to 40 °C yield under same conditions |
|---|---|---|---|---|---|---|
| 1 | Temp 80 | pH 10 | 50 | Min 10 | 996.695 | 863.78 % |
| 2 | Temp 80 | pH 10 | 5 | Min 10 | 687.075 | 647.43 % |
| 3 | Temp 80 | pH 7 | 50 | Min 10 | 919.083 | 921.57 % |
| 4 | Temp 80 | pH 7 | 5 | Min 10 | 972.796 | 677.91 % |
| 5 | Temp 80 | pH 4 | 50 | Min 10 | 880.269 | 691.56 % |
| 6 | Temp 80 | pH 4 | 5 | Min 10 | 937.582 | 756.57 % |
| 7 | Temp60 | pH 10 | 50 | Min 10 | ND | ND |
| 8 | Temp60 | pH 10 | 5 | Min 10 | 145.043 | 136.67 % |
| 9 | Temp60 | pH 7 | 50 | Min 10 | 912.469 | 914.94 % |
| 10 | Temp60 | pH 7 | 5 | Min 10 | 929.714 | 647.88 % |
| 11 | Temp60 | pH 4 | 50 | Min 10 | 866.391 | 680.66 % |
| 12 | Temp60 | pH 4 | 5 | Min 10 | 739.235 | 596.51 % |
| 13 | Temp 40 | pH 10 | 50 | Min 10 | 115.387 | 100 % |
| 14 | Temp 40 | pH 10 | 5 | Min 10 | 106.123 | 100 % |
| 15 | Temp 40 | pH 7 | 50 | Min 10 | 99.73 | 100 % |
| 16 | Temp 40 | pH 7 | 5 | Min 10 | 143.5 | 100 % |
| 17 | Temp 40 | pH 4 | 50 | Min 10 | 127.287 | 100 % |
| 18 | Temp 40 | pH 4 | 5 | Min 10 | 123.926 | 100 % |

Fig. 13

| # | Sample | Reducing agent | µg of total nucleic acid seq. | Mean 260/280 | Mean260/230 | Total µg nucleic acid seq. | indications | PCR Ct | PCR Target |
|---|---|---|---|---|---|---|---|---|---|
| 1 | M.luteus | Tris(hydroxy methyl)phosphine | 24.41 | 1.60 | 0.83 | **17.89** | - | - | - |
| 2 | M.luteus | Tris(hydroxy methyl)phosphine | 12.70 | | | | - | - | - |
| 3 | M.luteus | Tris(hydroxy methyl)phosphine | 16.56 | | | | - | - | - |
| 4 | M.luteus | TCEP | 14.59 | 1.67 | 1.03 | **14.71** | - | - | - |
| 5 | M.luteus | TCEP | 15.06 | | | | - | - | - |
| 6 | M.luteus | TCEP | 14.48 | | | | - | - | - |
| 7 | B.subtilis | Tris(hydroxy methyl)phosphine | 15.10 | 1.91 | 1.47 | **17.58** | - | 7.74 | Bac Univ 16S |
| 8 | B.subtilis | Tris(hydroxy methyl)phosphine | 17.39 | | | | - | 6.84 | Bac Univ 16S |
| 9 | B.subtilis | Tris(hydroxy methyl)phosphine | 20.24 | | | | - | 8.86 | Bac Univ 16S |
| 10 | B.subtilis | TCEP | 36.86 | 1.96 | 1.60 | **36.89** | - | 6.86 | Bac Univ 16S |
| 11 | B.subtilis | TCEP | 35.03 | | | | - | 6.78 | Bac Univ 16S |
| 12 | B.subtilis | TCEP | 38.78 | | | | - | 7.60 | Bac Univ 16S |
| 13 | M.luteus | Tris(hydroxy methyl)phosphine | 16.41 | 2.07 | 2.07 | **19.34** | 5min 37°C with Lysocyme | - | - |
| 14 | M.luteus | Tris(hydroxy methyl)phosphine | 20.62 | | | | 5min 37°C with Lysocyme | - | - |
| 15 | M.luteus | Tris(hydroxy methyl)phosphine | 20.98 | | | | 5min 37°C with Lysocyme | - | - |
| 16 | M.luteus | TCEP | 19.11 | 2.02 | 1.87 | **18.91** | 5min 37°C with Lysocyme | - | - |
| 17 | M.luteus | TCEP | 17.01 | | | | 5min 37°C with Lysocyme | - | - |
| 18 | M.luteus | TCEP | 20.61 | | | | 5min 37°C with Lysocyme | - | - |

Fig. 14

| sample | detergent | nucleic acid concentration (ng/uL) | A260/A280 | A260/A230 |
|---|---|---|---|---|
| 1 | SDS | 620 | 1.997 | 2.181 |
| 2 | SDS | 599 | 1.985 | 1.82 |
| 3 | SDS | 557 | 1.984 | 2.207 |
| 4 | SDS | 571 | 1.994 | 2.223 |
| 5 | LiDS | 589 | 2 | 2.247 |
| 6 | LiDS | 608 | 1.969 | 2.199 |
| 7 | LiDS | 470 | 1.985 | 2.153 |
| 8 | LiDS | 548 | 1.999 | 2.241 |
| 9 | Triton X-100 | 641 | 1.167 | 0.465 |
| 10 | Triton X-100 | 555 | 1.174 | 0.428 |
| 11 | Triton X-100 | 541 | 1.275 | 0.469 |
| 12 | Triton X-100 | 639 | 1.109 | 0.326 |

Fig. 15

| sample | detergent | nucleic acid concentration (ng/uL) | A260/A280 | A260/A230 |
|---|---|---|---|---|
| 1 | SDS | 62 | 1.716 | 1.862 |
| 2 | SDS | 63 | 1.697 | 1.888 |
| 3 | SDS | 63 | 1.677 | 1.782 |
| 4 | SDS | 93 | 1.722 | 1.571 |
| 5 | LiDS | 62 | 1.694 | 1.852 |
| 6 | LiDS | 102 | 1.769 | 1.54 |
| 7 | LiDS | 57 | 1.7 | 2.009 |
| 8 | LiDS | 65 | 1.752 | 1.933 |
| 9 | Triton X-100 | 155 | 0.476 | 0.127 |
| 10 | Triton X-100 | 213 | 0.465 | 0.182 |
| 11 | Triton X-100 | 142 | 0.478 | 0.12 |
| 12 | Triton X-100 | 157 | 0.505 | 0.129 |

Fig. 16

ISOLATION OF NUCLEIC ACIDS AT ELEVATED TEMPERATURES

TECHNICAL FIELD OF THE INVENTION

The present invention relates to a method and use for isolating nucleic acids from a sample using a solution comprising a reducing agent, a buffering substance and an anionic detergent, at elevated temperatures. The present invention also relates to solutions comprising said components as well as a kit comprising said solutions. Among other things, the methods and composition of the invention are suitable for a very fast and reliable isolation of nucleic acids with sufficient purity and integrity from different cell samples.

CROSS-REFERENCE TO RELATED APPLICATIONS

This application is a U.S. National Phase application filed under 35 U.S.C. § 371 claiming benefit to International Patent Application No. PCT/EP2021/062856, filed on May 14, 2021, which is entitled to priority of EP Application No. 20174548.6, EP Application No. 20174550.2, and LU Application No. 101791, all filed on May 14, 2020, the disclosures of each of which are incorporated by reference herein in their entirety.

DESCRIPTION

Various methods for extracting nucleic acids have been known for a long time. Initially, solely chemical methods based on toxic reagents such as phenol and chloroform were used. These methods were characterized especially by their high demands on laboratory safety (toxicity, fire hazard, disposal of the chemicals), as well as a labour-intensive and time-consuming execution.

With the advent of silica technology in the 1980s, this changed as it became easier for the end user to carry out the method. However, the chemicals used in silica-based nucleic acid extraction (chaotropic salts, alcohols) are still hazardous substances that require safe handling and separate disposal. In addition, silica technology uses enzymatic digestion with proteinase K for many sample types, which is characterized by a long incubation time.

WO 2006/138444 A2 describes lysis and stabilization buffers using the non-ionic surfactant Triton X-100 as detergent. However, the non-ionic detergent Triton X-100 results in a poor amount of nucleic acids which are highly impure and characterized by an unfavorable A260/280 and A260/230 ratio. The authors of WO 2006/138444 A2 could not realize this deficiency since they neither quantified the nucleic acid concentration, nor provided any information about the purity of the obtained nucleic acid.

Thus, different methods for isolating nucleic acids from samples such as biological samples are known. Yet, there is still a need for alternative methods. Especially, there is a need for methods that allow rapid nucleic acid isolation from diverse samples and in which the amount and quality of the obtained nucleic acids is sufficient for diverse downstream applications such as nucleic acid amplifications methods such as RT-PCR, qPCR, sequencing methods such as Next Generation Sequencing, cloning methods, or the like. Especially, there is a need for methods that allow rapid nucleic acid isolation from samples without the need to apply a time-consuming enzymatic digestion step.

The present invention addresses these needs by providing compositions, uses and methods that are suitable among other things for a very fast and reliable isolation of nucleic acids with sufficient purity and integrity from different cell samples.

Within the scope of the inventor's research activities, various novel lysis methods for the isolation of nucleic acids were developed. Surprisingly, an enzyme-free (purely chemical) method based on reducing agents such as for example the chemical TCEP (or similar phosphine compounds) and anionic detergents such as SDS at elevated temperatures was identified, which has both a low toxicity of the chemicals involved, is extremely efficient, fast and easy to perform and results in nucleic acids with sufficient purity and integrity. This new method reduces the time for nucleic acid isolation to less than 15 minutes, which results in massive advantages for the end user compared to the state of the art.

The solution of the present invention is described in the following, exemplified in the examples, illustrated in the Figures and reflected in the claims.

The present invention relates to a use of a "solution" (in the following also denoted as "solution of the invention"), which comprises (a) a buffering substance, preferably for buffering the solution at a pH of about 1 to 13, more preferably at a pH of about 4-11 or 4-10, and even more preferably at a pH of about 6-9; and (b) a reducing agent according to formula (I)

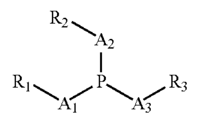

(I)

wherein $R_1$, $R_2$ and $R_3$ are independently selected from the group consisting of —H, —$OR_4$, —$COOR_5$, —$P(O)(OR_6)OR_7$, —$N(R_8)R_9$, —$S(O)_{0-2}R_{10}$, and —$SO_3H$;

$R_4$ to $R_{10}$ are independently selected from the group consisting of —H, and —$(C_1$-$C_{15})$alkyl;

$A_1$, $A_2$ and $A_3$, are independently selected from the group consisting of —$(C_1$-$C_{15})$alkylene-, —$(C_3$-$C_{10})$cycloalkylene-, —$(C_2$-$C_{15})$alkenylene-;

$A_1$, $A_2$ and $A_3$ optionally are further substituted with one or more substituents selected from —$OR_4$, —$COOR_5$, and —$(C_1$-$C_{15})$alkyl; and a salt thereof; and (c) preferably an anionic detergent, for isolating nucleic acids from a sample at a temperature of at least about 60° C., preferably for at least 10 seconds.

The present invention also relates to an in vitro method for isolating nucleic acids from a sample, wherein said method makes use of the solution of the invention.

The present invention also relates to a use of the solution of the invention, which optionally further comprises (d) less than 1 M of a chaotropic salt (CAO) and/or urea and/or thiourea; for isolating nucleic acids from a sample. Said solution of the invention which optionally further comprises (d) less than 1 M of a chaotropic salt (CAO) and/or urea and/or thiourea may also be employed in an in vitro method of the invention which is for isolating nucleic acids from a sample.

The present invention also relates to the solution of the invention as defined herein and further to the solution of the invention as defined herein for use in a method or use as disclosed herein.

Further, the present invention relates to the solution of the invention as defined herein for use in a method or use as disclosed herein, wherein said solution of the invention may optionally further comprise less than 1 M of a chaotropic salt (CAO) and/or urea and/or thiourea and wherein the solution has a temperature of at least about 60° C.

The present invention also relates to a kit comprising a solution as described herein, particularly the solution of the invention.

The Figures show:

FIG. 1 shows the gel electrophoresis performed with the different samples used in Example 1, which are depicted in FIG. 1. The gel in FIG. 1A reflects nucleic acids obtained by sample 1 and 2. The gel depicted in FIG. 1B shows nucleic acids obtained by sample 3, 4, 5, 6, and 7. As evident from FIG. 1, all samples provide for a high-molecular-weight band with no low-molecular-weight smears indicating that only low or no amounts of degraded nucleic acids are present in the tested samples.

FIG. 2 shows the gel electrophoresis on the nucleic acids obtained in Example 2. The gel obtained by gel electrophoresis performed with the different samples used in this experiment is depicted in FIG. 2 (nucleic acids obtained by sample 1, 2, 3, 4, 5, and 6 in the respective lanes). As evident from FIG. 2 all samples provide for a high-molecular-weight band indicating that intact (non-degraded) nucleic acids are present in the tested samples. The low-molecular-weight smears seem to be higher in the acidic conditions than in the alkaline conditions. Thus, the amount of degraded nucleic acids may be higher under acidic conditions than in alkaline conditions.

FIG. 3 shows the gel electrophoresis of the nucleic acids obtained in Example 3. The gel obtained by gel electrophoresis performed with the different samples used in this experiment is depicted in FIG. 3A (nucleic acids obtained by sample 1, 2, 3, 4, 5, and 6 in the respective lanes). As evident from FIG. 3A all samples provide for a high-molecular-weight band indicating that intact (non-degraded) nucleic acids are present in the tested samples. Further, the amount of nucleic acids obtained by the TCEP lysis are clearly higher than the amount obtained by a lysis including enzymatic digestion. The according PCR graph is depicted in FIG. 3B. The RT-PCR was performed on nucleic acids obtained in Example 3. These data confirm that the amount of nucleic acids obtained by the "TCEP lysis" is higher than the amount of nucleic acids obtainable by the standard lysis including a step of enzyme digestion.

FIG. 4 shows the photometric measurements performed in Example 14 for gram negative bacteria. For samples 1-4 of Example 14 for gram negative bacteria, the respective photometric measurement is shown in FIG. 4A. For samples 5-8 of Example 14 for gram negative bacteria, the respective photometric measurement is shown in FIG. 4B. For samples 9-12 of Example 14 for gram negative bacteria, the respective photometric measurement is shown in FIG. 4C.

FIG. 5 shows the results of the gel electrophoresis performed in Example 14 for gram negative bacteria. The following numbering applies: lines 1-4: Sodium-dodecylsulfat (SDS); lines 5-8: Lithium-dodecylsulfat (LiDS); lines 9-12: Triton X-100; and line 13: DNA Ladder GeneRuler 1 KB+.

FIG. 6 shows the photometric measurements performed in Example 14 for human blood. For samples 1-4 of Example 14 for human blood, the respective photometric measurement is shown in FIG. 6A. For samples 5-8 of Example 14 for human blood, the respective photometric measurement is shown in FIG. 6B. For samples 9-12 of Example 14 for human blood, the respective photometric measurement is shown in FIG. 6C.

FIG. 7 shows the results of the gel electrophoresis performed in Example 14 for human blood. The following numbering applies: lines 1-4: Sodium-dodecylsulfat (SDS); lines 5-8: Lithium-dodecylsulfat (LiDS); lines 9-12: Triton X-100; and line 13: DNA Ladder GeneRuler 1 KB+.

FIG. 8 shows Table 5B.

FIG. 9 shows Table 8: Results obtained for lysis with lysis buffer including different reducing agents without enzyme digestion.

FIG. 10 shows Table 9: Results obtained for lysis with lysis buffer including different reducing agents without enzyme digestion.

FIG. 11 shows Table 10: Results obtained for lysis with lysis buffer including different reducing agents without enzyme digestion.

FIG. 12 shows Table 11: Results obtained for lysis with lysis buffer excluding SDS or TCEP.

FIG. 13 shows Table 12: Results obtained for lysis with lysis buffer of different parameters.

FIG. 14 shows Table 14: Results obtained for lysis with lysis buffer including different reducing agents. Lys means that an additional lysozyme step was present.

Figures 1A, 1B:
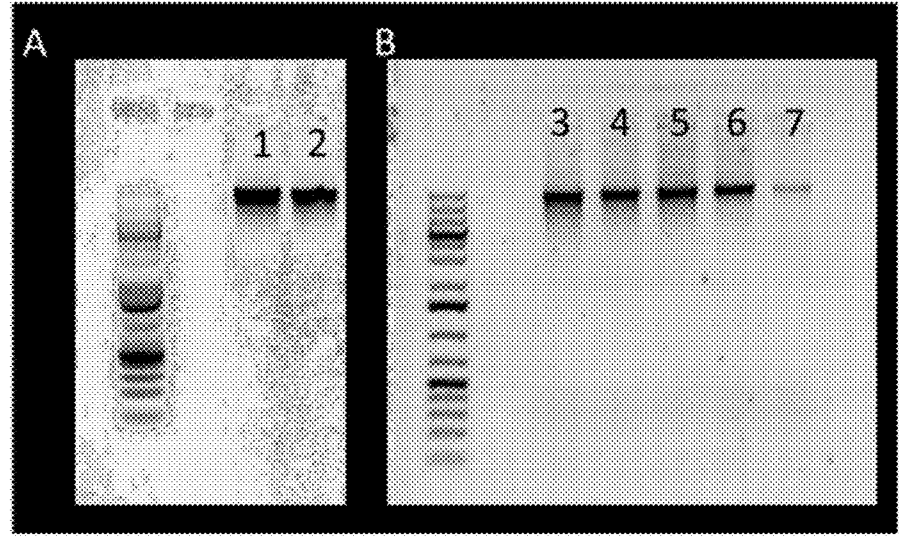

FIG. 15 shows Table 15: Results obtained for samples with different detergents with regard to nucleic acid concentration, A260/A280 and A260/A230. Shading without circles shows samples with high A260/A280 and/or A260/A230 ratios. Shading with circles shows samples with low A260/A280 and/or A260/A230 ratios.

FIG. 16 shows Table 16: Results obtained for samples with different detergents with regard to nucleic acid concentration, A260/A280 and A260/A230. Shades boxes without a circle shows samples with high A260/A280 and/or A260/A230 ratios. Circled shaded boxes show samples with low A260/A280 and/or A260/A230 ratios.

It was surprisingly found that when using a solution including a reducing agent (b) as disclosed herein, a buffering substance (a) and an anionic detergent (c) as described herein, nucleic acids are obtainable from diverse types of samples in a sufficient amount and with good quality in about 15 minutes or less, preferably 10 minutes or less, more preferably 5 minutes or less. The buffering substance (a) is preferably for buffering the solution at a pH of about 6-9, preferably at about 7.5.

It will be understood that the term "about" in the context of a value also includes the value as such. It will be further understood that the term "about" in the context of a pH value refers to the value as such and + or − or +/−10%.

It is envisioned that the reducing agent (b) is present in the solution in a concentration from about 20 mM to 100 mM, preferably at about 50 mM. The sample in the inventive solution as described herein may be incubated at at least about 60° C., preferably at a temperature in the range from about 60° C. to about 85° C., more preferably at about 80° C. The preferred reducing agent (b) is TCEP, while SDS and LiDS are preferred anionic detergents (c). It is further preferred that in the context of the uses and methods and kits of the present invention, a clearing solution (h) may be added to the solution, wherein said clearing solution precipitates the anionic detergent. Said clearing solution may therefore comprise K+, Rb+, Cs+, Mg++, Ca++, Sr++ or Ba++. Preferably, the cation may be Mg++, Ca++, Sr++ or Ba++. More preferably, the cation may be Ca++, Sr++ or Ba++. Still more preferably, the cationic ion may be Ca++ or Sr++. Even more preferably, the cation is Sr++. The clearing solution comprises in another preferred embodiment SrCl. It will be understood that the addition of the clearing solution aims at the addition of compounds which precipitate the anionic detergent—the term "clearing solution" thus also encompasses the addition of solid precipitating compounds, e.g. SrCl.

Additionally, it is preferred that the solution, particularly the solution of the invention, described herein and as employed in the methods and uses described herein comprises further optional components, like a chaotropic salt (d), a complexing agent (e), a compound, which provides $OH^-$ ions in solution (f), and/or a DNA stabilizer (g).

It was surprisingly found that for isolating nucleic acids from different types of sample, the time-consuming step of protease digestion can be omitted from the methods described herein which results in a very fast and reliable isolation of nucleic acids with sufficient purity and integrity from different cell samples. Table 12 of the appended examples illustrates that when the lysis of the sample is performed with the solution of the invention at a temperature of at least about 60° C., nucleic acids in sufficient amounts and quality are obtained. It is therefore preferred that the sample in the solution as described herein is incubated at a temperature of at least about 60° C., more preferably at a temperature in the range from about 60° C. to about 85° C., and even more preferably at about 80° C.

In the context of the present invention and as used herein, the term "about" followed by a temperature value means the temperature value as such +/−5° C., preferably +/−2° C. and more preferably +/−1° C. of that temperature value.

By this way, nucleic acids are obtainable in a sufficient quality and amount in a short period of time, for example about 15 minutes or even less, preferably in about 10 minutes or even less. Notably, the combination of the reducing agent with heat dramatically increases the amount of nucleic acids that can be obtained by the methods and the uses of the present invention as described in more detail in Example 10. In most cases, the amount of nucleic acids can be increased by at least 6× when increasing the temperature from 40° C. to 60° C. or 80° C. These data suggest that the reducing agent and the increase in temperature synergistically improve the isolation of nucleic acids. The presence of a chaotropic salt (CAO) and/or urea and/or thiourea in the solution is not necessary to obtain nucleic acids when the solution including the sample is incubated with heat.

The presence of a chaotropic salt and/or urea and/or thiourea is optional and may be tolerated (provided that the amount of the chaotropic is such that it does not precipitate the anionic detergent), although these components are not necessary for the uses, methods, solutions and kits of the present invention. Therefore, it is also possible (but less preferred) that nucleic acids are isolated when the solution comprises a chaotropic salt and/or urea and/or thiourea.

As already mentioned herein above and elsewhere, it was surprisingly found that for isolating nucleic acids from different types of sample, the time-consuming step of protease digestion can be omitted. It is thus preferred that the methods and uses as described herein do not include a step of contacting the sample with an enzyme (like those described herein in more detail) that is typically used in the art in the context of nucleic acid isolation methods.

It is likewise preferred that the solution and kits of the invention may not comprise such an enzyme. Accordingly, it is preferred that the methods and uses described herein do not include a step of performing lysis with an enzyme.

The mentioned "enzyme" includes enzymes that are typically used in nucleic acid isolation methods, such as proteases, lysozymes, lipases, cellulases, hydrolases, chitinases, amylases or glucanases.

Exemplary proteases include subtilisins, subtilases and alkaline serine proteases. Exemplary subtilisins include proteinase K, proteinase R, proteinase T, subtilisin A, subtilisin B or thermitase.

The methods/uses as described herein enables the isolation of the nucleic acids in less 30 minutes, preferably in less than 15 minutes, more preferably in less than 10 minutes, such as less than 5 minutes, less than 4 minutes, less than 3 minutes, less than 2 minutes, less than 1 minute, or even less than 30 seconds.

Accordingly, it is preferred that the methods/uses allow for isolation of nucleic acids within 10 minutes or less, and most preferred that the methods/uses allow for isolation of nucleic acids within 5 minutes or less.

It is preferred that the above time limits refer to the lysis step of the uses/methods of the invention. The measurement of the time limits is thus preferably calculated from the start of contacting the sample with the solution as defined herein.

It is also envisaged that the methods/uses of the present invention do not include a step of contacting the sample with a chaotropic salt and/or urea and/or thiourea at a concentration of 100 mM or 200 mM or more. It is also envisaged that the solution as disclosed herein does not comprise a chaotropic salt and/or urea and/or thiourea at a concentration of 100 mM or 200 mM or more. As shown in the Examples for obtaining nucleic acids in a sufficient amount and at sufficient quality, the lysis solution as described herein does not require the presence of chaotropic salts or urea at all.

The same holds true for the addition of a compound that provides for $OH^-$ ions in solution (compound (f)). Thus, the solution as disclosed herein may or may not comprise a compound that provides for $OH^-$ ions in solution (f).

It is also contemplated that the nucleic acids that are to be isolated remain in solution during all method steps or uses as described herein. Consequently, it is further contemplated that the nucleic acids are present in the eluate e.g. obtained by step (iii). Step (iii) is a step separating non-nucleic acid components from nucleic acids, as further detailed herein below.

The amount and quality of the nucleic acids as obtained by the methods/uses as described herein is sufficient so that these nucleic acids can be used in diverse downstream applications. Thus, the isolated nucleic acids/eluate (including the isolated nucleic acids in solution) can be analyzed by all conventional molecular techniques such as for example PCR, next generation sequencing, SNP genotyping, qPCR or RT-PCR. The isolated nucleic acids can therefore be analyzed (subsequently to their isolation) by methods such as PCR next generation sequencing, SNP genotyping or RT-PCR without the need of further isolating steps.

It is further contemplated that the nucleic acids are not precipitated by the addition of organic solvents in the methods/uses as described herein. Thus, the methods/uses as described herein may not include a step of contacting the sample with an organic solvent. Organic solvents, which effect precipitation of nucleic acids are known to a person skilled in the art may include, e.g., alcohols such as methanol, ethanol or propanol.

The term "isolating" or "isolation" (or the like) of nucleic acids as used herein means the purification of nucleic acids. For example, the isolating or isolation may mean that the nucleic acids are extracted from the sample. It is envisioned that the extraction of the nucleic acids from the sample can include that the nucleic acids are brought into solution. The term "brought into solution" means that the nucleic acids are isolated from the sample such as e.g. cells, cell nucleus or proteins and can be present (at least partially) separately from these components in solution. It is preferred that the term "isolating" or "isolation" of nucleic acids excludes the mere lysis of cell samples.

Nucleic acids as described herein may refer to any nucleic acid. For example, the nucleic acid may be RNA or DNA, preferably DNA. RNA as used herein may refer to any RNA. The RNA may be mRNA, tRNA, or rRNA. The DNA may be genomic DNA, circulating DNA or plasmid DNA.

The present methods/uses relate to the isolation of nucleic acids from a sample. The sample may be any suitable sample. For example, the sample may be any sample comprising nucleic acids. The sample can be a sample comprising or being suspected to comprising cells, virus, viroids or plasmids.

The sample can thus be a biological sample. As such the sample may be a sample obtained from an animal, plant, microorganism, virus, protozoa, chromista or fungi. It is also envisioned that the sample is a blood sample, preferably a human blood sample, or a tissue sample, preferably a muscle sample, sperm sample, plant sample, cell sample, mucosa sample, such as an oral mucosa sample or a bacterial sample, preferably a gram-negative bacterial sample.

Also envisioned are environmental samples. An environmental sample may be a water sample, earth sample, air sample, preferably these samples comprise or are suspected of comprising cells, virus, viroids or plasmids.

The sample is described to be contacted with a solution comprising (a) a buffering substance (BU), (b) a reducing agent (RA) and (c) preferably an anionic detergent; and optionally the further components as described herein.

It is preferred that the reducing agent (b) is a compound according to formula (I):

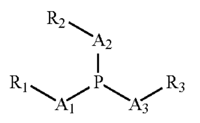
(I)

wherein $R_1$, $R_2$ and $R_3$ are independently selected from the group consisting of —H, —$OR_4$, —$COOR_5$, —$P(O)(OR_6)OR_7$, —$N(R_8)R_9$, —$S(O)_{0-2}R_{10}$, and —$SO_3H$;

$R_4$ to $R_{10}$ are independently selected from the group consisting of —H, and —($C_1$-$C_{15}$)alkyl;

$A_1$, $A_2$ and $A_3$, are independently selected from the group consisting of —($C_1$-$C_{15}$)alkylene-, —($C_3$-$C_{10}$)cycloalkylene-, —($C_2$-$C_{15}$)alkenylene-;

$A_1$, $A_2$ and $A_3$ optionally are further substituted with one or more substituents selected from —$OR_4$, —$COOR_5$, and —($C_1$-$C_{15}$)alkyl; and a salt thereof.

The methods/uses as described herein include the step of contacting the sample with a solution comprising inter alia a reducing agent (b), preferably a reducing agent of the formula (I), as defined herein.

Generally, any suitable reducing agent, preferably a reducing agent being of formula (I), can be used in the lysis solution as described herein. The skilled person knows suitable reducing agents having formula (I).

It is also preferred that in formula (I)

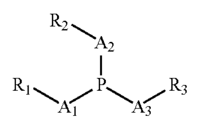
(I)

i) $R_1$, $R_2$ and $R_3$ are independently selected from the group consisting of —H, —$OR_4$, —$COOR_5$, —$P(O)(OR_6)OR_7$, —$S(O)_{0-2}R_{10}$, and —$SO_3H$, preferably from H, —OH, and —COOH and/or ii) $R_4$ to $R_{10}$ are —H, and/or iii) $A_1$, $A_2$ and $A_3$, are independently selected from the group consisting of —($C_1$-$C_9$)alkylene-, —($C_3$-$C_9$)cycloalkylene-, —($C_2$-$C_9$)alkenylene-;

preferably —($C_1$-$C_5$)alkylene-, —($C_3$-$C_6$)cycloalkylene-, —($C_2$-$C_5$)alkenylene- and/or iv) $A_1$, $A_2$ and $A_3$, are independently selected from the group consisting of —($C_1$-$C_9$)alkylene- and —($C_2$-$C_9$)alkenylene-, preferably —($C_1$-$C_5$)alkylene-, and —($C_2$-$C_5$)alkenylene)-, more preferably —($C_1$-$C_3$)alkylene-, and —($C_1$-$C_3$)alkenylene- and/or v) $A_1$, $A_2$ and $A_3$ optionally are further substituted with one or more substituents selected from —$OR_4$ or ($C_1$-$C_{15}$)alkyl, preferably ($C_1$-$C_{15}$)alkyl.

In a further embodiment, in formula (I), $R_1$, $R_2$ and $R_3$ are independently selected from the group consisting of H, —$OR_4$ and —$COOR_5$; wherein $R_4$ and $R_5$ are independently selected from the group consisting of —H, and —($C_1$-$C_{10}$)alkyl, preferably —($C_1$-$C_5$)alkyl; and $A_1$, $A_2$ and $A_3$ are independently selected from the group consisting of —($C_1$-$C_5$)alkylene-.

In another embodiment, in formula (I), $R_1$, $R_2$ and $R_3$ are independently selected from the group consisting of H, —$OR_4$ and —$COOR_5$; wherein $R_4$ and $R_5$ are H, and $A_1$, $A_2$ and $A_3$ are independently selected from the group consisting of —($C_1$-$C_5$)alkylene-, preferably —($C_1$-$C_3$)alkylene-.

Thus, it is contemplated that the reducing agent according to formula (I) may be selected from the group consisting of Tris(2-carboxyethyl)phosphine (TCEP), Tris(hydroxy methyl)phosphine, Tris(hydroxyethyl)phosphine and Tris(hydroxypropyl)phosphine.

In a preferred embodiment, in formula (I), $R_1$, $R_2$ and $R_3$ are each COOH, and $A_1$, $A_2$ and $A_3$ are independently selected from the group consisting of —($C_1$-$C_5$)alkylene-, preferably —($C_1$-$C_3$)alkylene-. Most preferably, in formula (I), $R_1$, $R_2$ and $R_3$ are each COOH, and $A_1$, $A_2$ and $A_3$ are each —$(CH_2)_2$—.

Accordingly, in the most preferred embodiment, the reducing agent (b) according to formula (I) is Tris(2-carboxyethyl)phosphine (TCEP).

The term "alkyl" refers to a monoradical of a saturated straight or branched hydrocarbon. Preferably, the alkyl group comprises from 1 to 15 (such as 1 to 10) carbon atoms, i.e., 1, 2, 3, 4, 5, 6, 7, 8, 9, 10, 11, 12, 13, 14 or 15 carbon atoms. For example, the term "($C_1$-$C_{15}$)alkyl" represents an alkyl group with 1 to 15 carbon atoms. More preferably, the alkyl group comprises 1 to 8 carbon atoms, most preferably 1 to 5 carbon atoms, even more preferred 1 to 4 carbon atoms. Exemplary alkyl groups include methyl, ethyl, propyl, iso-propyl, butyl, iso-butyl, tert-butyl, n-pentyl, iso-pentyl, sec-pentyl, neo-pentyl, 1,2-dimethyl-propyl, isoamyl, n-hexyl, iso-hexyl, sec-hexyl, n-heptyl, iso-heptyl, n-octyl, 2-ethyl-hexyl, n-nonyl, n-decyl, n-undecyl, n-dodecyl, and the like.

The term "alkylene" refers to a diradical of a saturated straight or branched hydrocarbon. Preferably, the alkylene comprises from 1 to 15 carbon atoms, i.e., 1, 2, 3, 4, 5, 6, 7, 8, 9, 10, 11, 12, 13, 14 or 15 carbon atoms. For example, the term "—$(C_1-C_{15})$alkylene-" represents an alkylene group with 1 to 15 carbon atoms. More preferably, the alkylene group comprises 1 to 9 carbon atoms, most preferably 1 to 5 carbon atoms. Exemplary alkylene groups include methylene, ethylene (i.e., 1,1-ethylene, 1,2-ethylene), propylene (i.e., 1,1-propylene, 1,2-propylene (—$CH(CH_3)CH_2$—), 2,2-propylene (—$C(CH_3)_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1-iso-pentylene, 1,1-sec-pentyl, 1,1-neo-pentyl), the hexylenisomers (e.g., 1,1-hexylene, 1,2-hexylene, 1,3-hexylene, 1,4-hexylene, 1,5-hexylene, 1,6-hexylene, and 1,1-isohexylene), and the like.

The term "cycloalkylene" refers to a non-aromatic diradical of a saturated or partially unsaturated cyclic straight or branched hydrocarbon. Preferably, the cycloalkylene comprises from 3 to 10 carbon atoms, i.e., 3, 4, 5, 6, 7, 8, 9, or 10 carbon atoms. For example, the term "—$(C_1-C_{10})$cycloalkylene-" represents an cycloalkylene group with 1 to 10 carbon atoms. More preferably, the cycloalkylene group comprises 3 to 9 carbon atoms, most preferably 3 to 6 carbon atoms. Exemplary cycloalkyl groups include cyclopropylene, cyclopropenylene, cyclobutylene, cyclobutenylene, cyclopentylene, cyclopentenyenel, cyclohexylene, cyclohexenylene, cycloheptylene, cycloheptenylene, cyclooctylene, cyclooctenylene, cyclononylene, cyclononenylene, cylcodecylene, cylcodecenylene, and adamantly. The term "cycloalkylene" is also meant to include bicyclic and tricyclic versions thereof. If bicyclic rings are formed, it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkylene include —$(C_3-C_9)$cycloalkylene, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl.

The term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 4, i.e., 1, 2, 3, or 4, carbon-carbon double bonds. Preferably, the alkenylene group comprises from 2 to 15 carbon atoms, i.e., 2, 3, 4, 5, 6, 7, 8, 9, 10, 11, 12, 13, 14 or 15 carbon atoms. For example, the term "—$(C_2-C_{15})$alkenylene-" represents an alkenylene group with 2 to 15 carbon atoms. More preferably, the alkenylene group comprises 2 to 9 carbon atoms, most preferably 2 to 5 carbon atoms, particularly preferred 2 to 3 carbon atoms. Thus, in a preferred embodiment, the alkenylene group comprises from 2 to 15 carbon atoms and 1, 2, 3, 4, 5, 6 or 7 carbon-carbon double bonds, more preferably, it comprises 2 to 9 carbon atoms and 1, 2, 3 or 4 carbon-carbon double bonds, most preferably 2 to 5 carbon atoms and 1 or 2 carbon-carbon double bonds, particularly preferred 2 to 3 carbon atoms and 1 carbon-carbon double bond. The carbon-carbon double bond(s) may be in cis (Z) or trans (E) configuration. Exemplary alkenylene groups include ethen-1,2-diyl, vinyliden, 1-propen-1,2-diyl, 1-propen-1,3-diyl, 1-propen-2,3-diyl, allyliden, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like.

The reducing agent (RA) may be present in the solution in any suitable amount. For example, the reducing agent as used in the methods as described herein may be present in a concentration of at least 1 mM, 2 mM, 5 mM, 10 mM, 20 mM, 30 mM, 40 mM, 50 mM, 60 mM, 70 mM, 80 mM, 90 mM, 100 mM, 110 mM, 120 mM, 130 mM, 140 mM, 150 mM, 160 mM, 170 mM, 180 mM, 190 mM, 200 mM, 500 mM or more. The reducing agent may also be present in a concentration of about 1 mM to 500 mM. The reducing agent may be present in a concentration of about 1 mM to about 200 mM or 2 mM to 150 mM, preferably in a concentration of 5 mM to 140 mM, more preferably in a concentration of about 10 mM to about 100 mM, still more preferably in a concentration of about 10 mM to about 50 mM or 10 mM to 40 mM. The reducing agent may also be present in a concentration of 5 mM to 100 mM, more preferably in a concentration of about 10 mM to about 100 mM, most preferably in a concentration of about 10 mM to about 50 mM, even more preferably in a concentration of about 20-40 mM. The reducing agent may also be present in a concentration of about 1 mM to about 200 mM. The reducing agent may also be present in a concentration of about 30 mM to about 50 mM. The reducing agent may also be present in a concentration of 20 mM The reducing agent may also be present in a concentration of 30 mM. The reducing agent may also be present in a concentration of 40 mM. The reducing agent may also be present in a concentration of 50 mM. The reducing agent may also be present in a concentration of 100 mM.

It is preferred that the reducing agent (b) as used in the methods as described herein is present in a concentration of about 20 mM to about 100 mM, more preferably the reducing agent (b) is present in a concentration of about 50 mM.

It is also contemplated that the sample is contacted with a solution, the solution comprising the buffering substance, the reducing agent and preferably an anionic detergent as described herein.

The buffering substance (BU) can be any suitable buffering substance. Principally, a buffering substance resists a certain change in pH upon dilution or in addition of small amounts of acids or alkali. The buffering agent should for example be able to buffer in a pH range in between a pH of about 1-13, preferably 2-13, more preferably 4-11 or 4-10, even more preferably 4-7 or 5-8 or 6-9. The buffering agent can also be able to buffer in a pH range of about 3 and about 11, preferably in a pH range of about 4 to about 10. It is preferred that the buffering substance is able to buffer in a pH range in between a pH of about 6 to about 9, most preferably at a pH of about 7.5. It goes without saying that the above pH values ranges may be employed in all embodiments of the present invention.

Buffering substances (BU) are well-known to the skilled person and can be selected from the group comprising or consisting of TRIS, such as TRIS-HCl, tartrate buffer, borate buffer, carbonate buffer, citrate buffer, HEPES, HPPS, MES ([2-(N-morpilino)ethanesulfonic acid]), ADA (N-2-acetamido-2-iminodiaceitic acid), AMP, AMPSO, CAPSO, CAPS, CABS, CHES, PIPES, ACES, MOPSO, MOPS, BES, TES, DIPSO, TAPSO, TEA, EPS, HEPBS, POPSO, HEPPSO, HEPPS, TAPS, cholamine chloride buffer, acetamidoglycine buffer, tricine buffer, glycinamid buffer, glycylglycine buffer, bis-tris methane buffer, bicin buffer, or any ammonia buffer, preferably the buffer substance is TRIS, preferably TRIS-HCl or tartrate buffer, preferably sodium tartrate.

In one preferred embodiment, the buffering substance (BU) is TRIS.

In one more preferred embodiment, the buffering substance (BU) is TRIS-HCl.

In one preferred embodiment, the buffering substance (BU) is a tartrate buffer.

In one more preferred embodiment, the buffering substance (BU) is sodium tartrate.

The sample may be contacted with a solution comprising a buffering substance (a) in any suitable amount. For example, the buffering substance (a) may be present in a concentration of at least about 2 mM, 5 mM, 10 mM, 20 mM, 30 mM, 40 mM, 50 mM, 60 mM, 70 mM, 80 mM, 90 mM, 100 mM or more. It is further envisioned that the buffering substance (BU) can be present in a concentration of about 2 mM to about 50 mM, preferably in a concentration of about 5 mM to about 40 mM, more preferably in a concentration of about 10 mM to about 30 mM. For example, the buffering substance may be present in a concentration of about 20 mM or 50 mM. Thus, the buffering substance (BU) may be TRIS such as TRIS-HCl and wherein TRIS is present in a concentration of about 2 mM to about 50 mM, preferably in a concentration of about 5 mM to about 40 mM, more preferably in a concentration of about 10 mM to about 30 mM.

The buffering substance may be tartrate (as mentioned herein before). Tartrate may be present in a concentration of about 2 mM to about 50 mM, preferably in a concentration of about 5 mM to about 40 mM, more preferably in a concentration of about 10 mM to about 30 mM, most preferably about 20 mM.

The solution as disclosed herein also comprises a detergent (c).

The detergent to be employed in the context of all embodiments of the present invention may be any suitable detergent, and in particular any suitable anionic detergent.

Non-limiting examples of detergents can include, but are not limited to, sodium dodecyl sulfate (SDS, or sometimes also denoted as NaDS), lithium dodecyl sulfate (LiDS), 3-[(3-cholamidopropyl)dimethylammonio]-1-propanesulfonate (CHAPS) and 3-[(3-cholamidopropyl)dimethylammonio]-2-hydroxy-1-propanesulfonate (CHAPSO).

Non-limiting examples of anionic detergents include lithium dodecyl sulfate (LiDS), NaDS, sodium octyl sulfate, decyltrimethylammonium chloride, potassium oleate, sodium pentanesulfonate, sodium dodecyl sulfate, butylnaphthalensulfonic acid sodium salt, 4-morpholineethanesulfonic acid, sodium decyl sulfate, lignosulfonic acid calcium salt, sodium 1-butanesulfonate, sodium dodecylbenzenesulphonate, sodium stearate, magnesium stearate, 1-dodecanesulfonic acid sodium salt, sodium allylsulfonate, 3-(N,N-dimethylpalmitylammonio)propanesulfonate, sulfonated castor oil, 2,6-dimorpholin-4-ylpyrimidine-4-carboxylic acid, disodium methylenebisnaphthalenesulphonate, sodium alkylbenzene sulfonate, hydroxyaluminum distearate, sodium ethyl 2-sulfolaurate, sodium diisobutyl sulfosccinate, dodecylbentenesulfonic acid sodium salt, dicyclohexyl sulfosuccinate sodium salt, disodium 4-dodecyl-2,4'-oxydibenzenesulfonate, sulfonated aliphatic polyester, sodium-n-methyl-n-oleyl taurate, di-n-sodium sulfosuccinate, dibasic lead stearate, sodium n-octylsufonate, dodecyl triethanolamine sulfate, sodium diamyl sulfosuccinate, manganous stearate, calcium dodecylbenzene sulfonate, disodium 4-[2-[(1-oxoundec-10-enyl)amino]ethyl]2-sulphonatosuccinate, sodium poly[(naphthaleneformaldehyde)sulfonate], 1-hexadecanesulfonic acid sodium salt, ammonium lauryl sulfate, 1-pentanesulfonic acid sodium salt monohydrate, sodium lignosulfonate, dodecylbenzenesulphonic acid, sodium lauryl polyoxyethylene ether sulfate, sodium nonylphenol polyoxyethylene ether sulfate, sodium dodecyl sulfate, fatty alcohol ammonium sulfate, sodium oleyl sarcosinate, lauryl polyoxyethylene ether triethanol amine salt, dodecyl phenyl ammonium sulfate, sodium pyrrolidone carbonate, n-acyl glutamate potassium salt, sodium polyalkyl phenyl polyoxyethylene ether sulfate, stearyltoluene sodium sulfonate, nonylphenyl polyoxyethylene ether sulfate triethanolamine, glyceryl ethercarboxylic acid salt, calcium stearyl lactate, monoethanolamine dodecyl sulfate, alkoxy ethanolamido sulfosuccinate sodium salt, ammonium dodecylbenzenesulphonate, dodecay diethanol amine sulfate, sodium dibenzyl amine benzene sulfonate or sodium dibenzyl amine benzene sulfonate.

In one more preferred embodiment of any use, method or solution described herein, the anionic detergent is sodium dodecyl sulfate (SDS), lithium dodecyl sulfate (LiDS), ammonium dodecyl sulfate, monoethanolamine dodecyl sulfate, diethanolamine dodecyl sulfate, or triethanolamine dodecyl sulfate.

In one still more preferred embodiment of any use, method or solution described herein, the anionic detergent is sodium dodecyl sulfate (SDS), lithium dodecyl sulfate (LiDS), ammonium dodecyl sulfate, monoethanolamine dodecyl sulfate, or triethanolamine dodecyl sulfate.

In one still more preferred embodiment of any use, method or solution described herein, the anionic detergent is sodium dodecyl sulfate (SDS), lithium dodecyl sulfate (LiDS), or ammonium dodecyl sulfate.

In one still more preferred embodiment of any use, method or solution described herein, the anionic detergent is sodium dodecyl sulfate (SDS) or lithium dodecyl sulfate (LiDS).

In one even more preferred embodiment of any use, method or solution described herein, the detergent is sodium dodecyl sulfate (SDS).

It is envisioned that the sample is contacted with a detergent, e.g. an anionic detergent, in a concentration of less than 1M, less than 900 mM, less than 800 mM, less than 700 mM, less than 600 mM, less than 500 mM, less than 400 mM, less than 300 mM, less than 200 mM, less than 190 mM, less than 180 mM, less than 170 mM, less than 160 mM, less than 150 mM, less than 140 mM, less than 130 mM, less than 120 mM, less than 110 mM, less than 100 mM, less than 90 mM, less than 80 mM, less than 70 mM, less than 60 mM, less than 50 mM, less than 40 mM, less than 30 mM, less than 20 mM, less than 10 mM, less than 5 mM, less than 4 mM, less than 3 mM or less.

The detergent, e.g. an anionic detergent, may also be present in a concentration of about 1 mM to about 150 mM, about 2 mM to about 140 mM, about 3 mM to about 130 mM, about 4 mM to about 120 mM, about 5 mM to about 110 mM, or about 7 mM to about 110 mM, or about 10 mM to about 100 mM. The detergent may also be present in a concentration of about 20 mM to about 100 mM.

The solution as disclosed herein may, in addition to a reducing agent (b) and the buffering substance (a), optionally further comprise a complexing agent (e). Accordingly, in the methods and uses described herein the sample may be contacted with such solution further comprising a complexing agent (e). The complexing agent is preferably a chelating agent. The complexing agent may be any suitable complexing agent. Complexing with a chelating agent involves the formation or presence of two or more separate coordinate bonds between a polydentate (multiple bonded) ligand and a single central atom.

The complexing agent may be added to the lysis solution to inhibit the DNase activity.

Non-limiting examples of a complexing agent include ethylenediaminetetraacetic acid (EDTA), ethylene glycol-bis(β-aminoethyl ether)-N,N,N',N'-tetraacetic acid (EGTA), and ethylene diamine diacetic acid (EDDS). Also, the complexing agent may be tartaric acid or a salt thereof, such as sodium tartrate.

In one preferred embodiment, the complexing agent is ethylene glycol-bis(β-aminoethyl ether)-N,N,N',N'-tetraacetic acid (EGTA).

In one preferred embodiment, the complexing agent is ethylene diamine diacetic acid (EDDS).

In one preferred embodiment, the complexing agent is sodium tartrate.

It is most preferred that the complexing agent is ethylenediaminetetraacetic acid (EDTA).

The complexing agent may be present in any suitable concentration. For example, the complexing agent may be present in a concentration of less than 10 mM, less than 9 mM, less than 8 mM, less than 7 mM, less than 6 mM, less than 5 mM, less than 4 mM, less than 3 mM, less than 2 mM, less than 1 mM, less than 0.9 mM, less than 0.8 mM, less than 0.7 mM, less than 0.6 mM, less than 0.5 mM, less than 0.4 mM, less than 0.3 mM, less than 0.2 mM, less than 0.1 mM, less than 0.05 mM or less. It is also envisioned that the complexing agent may be present in a concentration of about 0.01 mM to about 1 mM, about 0.025 mM to about 0.75 mM, about 0.05 mM to about 0.5 mM, about 0.075 mM to about 0.25 mM, or about 0.1 mM.

The solution of the invention as described herein may in addition to the reducing agent (b), the buffering substance (a), the detergent (c) and optionally the complexing agent (e) optionally comprise a chaotropic salt (CAO) and/or urea and/or thiourea (optional compound (d) as described herein).

The chaotropic salt (CAO) may be any suitable chaotropic salt. Likewise, urea may be any suitable urea. A chaotropic salt typically is a compound, which disrupts the structure of, and denatures, macromolecules such as proteins and nucleic acids (e.g. DNA and RNA) by interfering with intermolecular interactions mediated by non-covalent forces such as hydrogen bonds, van der Waals forces, and hydrophobic effects. Similar effects are also expected for urea.

The chaotropic salt can comprise or provide for an ion selected from the group consisting of $NO_3^-$, $Br^-$, $ClO_4^-$, $ClO_3^-$, $C_3OOOO^-$, $SCN^-$, $K^+$, $Ba^+$, $Li^+$, $NH_4^+$, $Mg^{2+}$, $Ca^{2+}$, and guanidinium. Preferably, the chaotropic salt can comprise or provide for an anion selected from the group consisting of $NO_3^-$, $Br^-$, $ClO_4^-$, $ClO_3^-$, $Cl_3OOOO^-$, $SCN^-$, $Li^+$, $NH_4^+$, $Mg^{2+}$, and guanidinium. More preferably, the chaotropic salt can comprise or provide for an anion selected from the group consisting of $NO_3^-$, $Br^-$, $ClO_4^-$, $ClO_3^-$, $Cl_3OOOO^-$, $SCN^-$, $Li^+$, $NH_4^+$, and guanidinium.

Non-limiting examples of chaotropic salts (CAO) include NaBr, NaI, NaSCN, LiCI, LiBr, $NH_4Ac$, NaCl, guanidinium chloride, guanidinium hydrochloride, lithium perchlorate, sodium perchlorate, lithium acetate, magnesium chloride, guanidinium isothiocyanate or guanidinum isocyanate (GuSCN). Preferably, chaotropic salts may include NaBr, NaI, NaSCN, LiCI, LiBr, $NH_4Ac$, NaCl, guanidinium chloride, guanidinium hydrochloride, lithium perchlorate, sodium perchlorate, lithium acetate, guanidinium isothiocyanate or guanidinum isocyanate (GuSCN).

Non-limiting examples of urea include urea or a salt thereof.

It is also contemplated that the sample is contacted with or that the lysis solution as described herein comprises 1, 2, 3, 4, 5, 6 or more different chaotropic salts and/or urea and/or thiourea.

It is envisioned that the chaotropic salt and/or urea and/or thiourea (c) is present in a concentration of less than 0.9 M, less than 0.8 M, less than 0.7 M, less than 0.6 M, less than 0.5 M, less than 0.4 M, less than 0.3 M, less than 0.2 M, less than 0.1 M, less than 0.09 M, less than 0.08 M, less than 0.07 M, less than 0.06 M, less than 0.05 M, less than 0.04 M, less than 0.03 M, less than 0.02 M, less than 0.01 M, less than 0.009 M, less than 0.008 M, less than 0.007 M, less than 0.006 M, less than 0.005 M, less than 0.004 M, less than 0.003 M, less than 0.002 M, less than 0.001 M or less.

It is also contemplated that the sample is not contacted with a chaotropic salt and/or urea and/or thiourea. Accordingly, it is also contemplated that the solution does not comprise a chaotropic salt and/or urea and/or thiourea.

It is optional that the sample is contacted with an enzyme in the methods/uses as described herein, in particular in the lysis step.

In this context, as already described herein above, it is noted again that it is preferred to carry out the methods and uses without contacting the sample with an enzyme. E.g., after isolation of the nucleic acid, enzymes may be added. Accordingly, it is further envisioned that the solution comprising the reducing agent (b), the buffering substance (a), the anionic detergent (c) and optionally one or more of (d)-(h) does not comprise an enzyme.

It is also contemplated that the solution further comprises a compound that provides for $OH^-$ ions in solution (optional compound (f) in the lysis solution described herein). The compound that provides for $OH^-$ ions in solution may be any suitable compound that provides for $OH^-$ ions in solution. For example, the compound that provides for $OH^-$ ions in solution may be NaOH. For example, the compound that provides for $OH^-$ ions in solution may be used to adjust the pH, if deemed necessary.

Yet, this compound should preferably be present only in low amounts. Thus, the solution may comprise a compound that provides for $OH^-$ ions in solution (f), wherein this compound has a concentration of less than 0.1 M, 0.05 M, 0.005 M, 0.0005 M or less. It can also be that the solution as disclosed herein does not comprise a compound that provides for $OH^-$ ions in solution (optional component).

Preferably, the solution as disclosed herein may comprise or consist of (a) a reducing agent (RA) as defined herein, preferably a reducing agent (RA) according to formula (I);

(b) a buffering substance (BU), preferably for buffering the solution at a pH of about 1 to 13, more preferably at a pH of about 4-11, and even more preferably at a pH of about 6-9;

(c) an anionic detergent, preferably SDS, and (e) optionally a complexing agent (CA).

More preferably, the solution as disclosed herein may comprise or consist of (a) a reducing agent (RA) as defined herein, preferably a reducing agent (RA) according to formula (I);

(b) a buffering substance (BU), preferably for buffering the solution at a pH of about 1 to 13, more preferably at a pH of about 4-11, and even more preferably at a pH of about 6-9;

(c) an anionic detergent, wherein the anionic detergent is SDS, and (e) optionally a complexing agent (CA).

It is also envisioned that the solution as disclosed herein may comprise or consist of (a) a reducing agent (RA) as defined herein, preferably a reducing agent (RA) according to formula (I);

(b) a buffering substance (BU), preferably for buffering the solution at a pH of about 1 to 13, more preferably at a pH of about 4-11, and even more preferably at a pH of about 6-9;

(e) optionally a complexing agent (CA); and (d) optionally a chaotropic salt (CAO); and further (c) an anionic detergent, preferably SDS;

optionally this solution has a pH of about 1-13, preferably a pH of about 2-13, more preferably a pH of about 4-11, more preferably a pH of about 6-9, and most preferably a pH of about 7.5-8.

Preferably, the solution as disclosed herein may comprise or consist of (a) a reducing agent (RA) as defined herein, preferably a reducing agent (RA) according to formula (I);

(b) a buffering substance (BU), preferably for buffering the solution at a pH of about 1 to 13, more preferably at a pH of about 4-11, and even more preferably at a pH of about 6-9;

(e) optionally a complexing agent (CA);

(d) optionally a chaotropic salt (CAO); and (c) an anionic detergent, preferably SDS;

optionally this solution has a pH of about 1-13, preferably a pH of about 2-13, more preferably a pH of about 4-11, more preferably a pH of about 6-9, and most preferably a pH of about 7.5-8.

More preferably, the solution as disclosed herein may comprise or consist of (a) a reducing agent (RA) as defined herein, preferably a reducing agent (RA) according to formula (I);

(b) a buffering substance (BU), preferably for buffering the solution at a pH of about 1 to 13, preferably at a pH of about 4-11, and even more preferably at a pH of about 6-9;

(e) optionally a complexing agent (CA);

(d) optionally a chaotropic salt (CAO); and (c) an anionic detergent, wherein the anionic detergent is SDS;

optionally this solution has a pH of about 1-13, preferably a pH of about 2-13, more preferably a pH of about 4-11, more preferably a pH of about 6-9, and most preferably a pH of about 7.5-8.

It is also envisioned that the solution as disclosed herein may additionally comprise a DNA stabilizer (g). Accordingly, the sample may be contacted with a DNA stabilizer (g). The DNA stabilizer may be any suitable DNA stabilizer. DNA stabilizers may be ammonium salt(s) such as ammonium chloride, ammonium sulfate salt(s), or calcium chloride ($CaCl_2$). In a preferred embodiment, ammonium chloride is used as DNA stabilizer.

The DNA stabilizer may be present in the solution at a concentration of at least 1 M, at least 2 M, at least 5 M, at least 7.5 M, at least 10 M, or at least 15 M or more. Also, the DNA stabilizer may be present at a concentration of at least 20 M, at least 25 M, at least 30 M, at least 40 M, at least 15 M or more. The solution may also comprise a DNA stabilizing agent at a concentration of less than 500 mM, less than 450 mM, less than 400 mM, less than 350 mM, less than 300 mM, less than 250 mM, less than 200 mM, less than 150 mM, less than 100 mM, less than 75 mM, or less. It is also envisioned that the DNA stabilizing agent has a concentration of about 1 mM to about 500 mM, about 5 mM to about 400 mM, about 10 mM to about 300 mM, about 20 mM to about 120 mM, about 25 mM to about 75 mM. Preferably, the DNA stabilizing agent has a concentration of about 50 mM in the solution.

Preferably, a solution as disclosed herein may comprise:

(a) a reducing agent (RA) as defined herein, preferably a reducing agent of formula (I);

(b) a buffering substance (BU), preferably for buffering the solution at a pH of about 1 to 13, more preferably at a pH of about 4-11 and even more preferably at a pH of about 6-9;

(e) optionally a complexing agent (CA);

(c) an anionic detergent, more preferably SDS; and (g) optionally a DNA stabilizer.

Also, preferably, a solution as disclosed herein may comprise:

(a) a reducing agent (RA) as defined herein, preferably a reducing agent of formula (I);

(b) a buffering substance (BU), preferably for buffering the solution at a pH of about 1 to 13, more preferably at a pH of about 4-11 and even more preferably at a pH of about 6-9;

(e) a complexing agent (CA);

(d) optionally a chaotropic salt (CAO);

(g) optionally a DNA stabilizer; and (c) an anionic detergent, more preferably SDS.

The solution as described herein may have any pH, which pH is suitable for isolating nucleic acid sequences. For example, the solution can have a pH of about 1-13, preferably a pH of about 2-13, more preferably a pH of about 4-11, even more preferably a pH of about 5-8, and most preferably a pH of about 7.5-8. It is also envisioned that the solution can have a pH of about 5-9, preferably a pH of about 6-8, more preferably the pH is about 7 (6.5-7.5). It is also envisioned that the solution can have a pH of about 7.5-8.0. It is also envisaged that the solution can have a pH of 2-13, preferably of 4-11. In a preferred embodiment, the solution can have a pH of about 4-7. It is also envisaged that the solution can have a pH of 5-9, preferably 5-8, more preferably the pH is about 7 (6.5-7.5). It is also envisaged that the solution can have a pH of 3-6. It is also envisaged that the solution can have a pH of 8-10.

Preferably, the solution as described herein comprises about 1-500 mM reducing agent and/or has a pH of about 2-13.

More preferably, the solution as described herein comprises about 1-500 mM, even more preferably about 5-100 mM reducing agent and/or has a pH of about 4-11.

More preferably, the solution as described herein comprises about 5-100 mM reducing agent and/or has a pH of about 2-13, even more preferably of about 4-11.

Even more preferably, the solution as described herein comprises about 5-100 mM reducing agent and/or has a pH of about 5-8.

Even more preferably, the solution as described herein comprises about 10-40 mM reducing agent and/or has a pH of about 2-13, even more preferably a pH of about 4-11.

Even more preferably, the solution as described herein comprises about 10-40 mM reducing agent and/or has a pH of about 5-8.

The solution as disclosed herein may thus comprise:

(a) 10-80 mM, preferably about 50 mM of buffering substance, preferably TRIS;
(b) 1-500 mM, preferably 5-100 mM, more preferably 20-40 mM, most preferably about 50 mM of reducing agent as disclosed herein, preferably TCEP;
(e) optionally 0.001-1 mM, preferably about 0.1 mM complexing agent, preferably EDTA;
(c) 1-100 mM, preferably 20-100 mM, more preferably about 70 mM anionic detergent, preferably SDS; and
(g) optionally 10-75 mM, preferably about 50 mM of DNA stabilizer as disclosed herein preferably, ammonium chloride, optionally this solution has a pH of about 1-13, preferably a pH of about 2-13, more preferably a pH of about 4-11, most preferably a pH of about 5-8.

Preferably, the solution as disclosed herein comprises:

(a) 10-80 mM, preferably about 50 mM of buffering substance, wherein the buffering substance is TRIS;
(b) 1-500 mM, preferably 5-100 mM, more preferably 20-40 mM, most preferably about 50 mM of reducing agent, wherein the reducing agent is TCEP;
(e) optionally 0.001-1 mM, preferably about 0.1 mM complexing agent, wherein the complexing agent is EDTA;
(c) 1-100 mM, preferably 20-100 mM, more preferably about 70 mM anionic detergent, wherein the detergent is SDS; and
(g) optionally 10-75 mM, preferably about 50 mM of DNA stabilizer, wherein the DNA stabilizer is ammonium chloride, optionally this solution has a pH of about 1-13, preferably a pH of about 2-13, more preferably a pH of about 4-11, most preferably a pH of about 6-9.

Preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, optionally this solution has a pH of about 1-13, preferably a pH of about 2-13, more preferably a pH of about 4-11, most preferably a pH of about 6-9.

Preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, wherein this solution has a pH of about 1-13.

Preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, wherein this solution has a pH of about 2-13.

More preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, wherein this solution has a pH of about 4-11.

More preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, wherein this solution has a pH of about 6-9.

More preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, wherein this solution has a pH of about 5-8.

More preferably, the solution as disclosed herein comprises:

(a) 10-80 mM TRIS;
(b) 1-500 mM TCEP;
(e) optionally 0.001-1 mM is EDTA;
(c) 1-100 mM SDS; and
(g) optionally 10-75 mM ammonium chloride, wherein this solution has a pH of about 7.5-8.

As described above it is also contemplated that the isolating of nucleic acids from a sample is at a temperature of at least about 60° C., preferably at a temperature in the range of about 60° C. to about 85° C., more preferably at a temperature of about 80° C., preferably for at least 10 seconds.

Notably, the temperature is measured at normal temperature and pressure (NTP). At NTP a temperature of 20° C. (293.15 K, 68° F.) and an absolute pressure of 1 atm (14.696 psi, 101.325 kPa) is present. Pressure may be measured with a barometer. Temperature may be measured with a thermometer.

The incubation in step (ii) or the isolation of acids from the samples may be at a temperature of at least about 60° C., a temperature of at least about 70° C., a temperature of at least about 75° C. or a temperature of at least about 80° C. It is also envisioned that incubation in step (ii) or the isolation of acids from the samples may be at a temperature of about 60° C. to about 95° C. or of about 75° C. to about 85° C.

The incubation in step (ii) or the isolation of nucleic acids from the samples may be for 10 seconds, 15 seconds, 30 seconds, 1 minute, 2 minutes, 3 minutes, 4 minutes, 5 minutes, 6 minutes, 7 minutes, 8 minutes, 9 minutes, 10 minutes, 12 minutes, 15 minutes, 17 minutes, 20 minutes, 25 minutes, 30 minutes, 40 minutes, 50 minutes or 1 hour or more. It is also envisioned that incubation in step (ii) or the isolation of acids from the samples may be for 10 seconds, 15 seconds, 30 seconds, 1 minute, 2 minutes, 3 minutes, 4 minutes, 5 minutes, 6 minutes, 7 minutes, 8 minutes, 9 minutes, 10 minutes, 12 minutes, 15 minutes, 17 minutes, 20 minutes, 25 minutes, 30 minutes, 40 minutes, 50 minutes or 1 hour or more.

The incubation in step (ii) or the isolation of nucleic acids from the samples may be at most for 1 hour, 50 minutes, 40 minutes, 30 minutes, 25 minutes, 20 minutes, 17 minutes, 15 minutes, 12 minutes, 10 minutes, 9 minutes, 8 minutes, 7 minutes, 6 minutes, 5 minutes, 4 minutes, 3 minutes, 2 minutes or 1 minute. It is also envisioned that incubation in step (ii) or the isolation of acids from the samples may be for at most for 1 hour, 50 minutes, 40 minutes, 30 minutes, 25 minutes, 20 minutes, 17 minutes, 15 minutes, 12 minutes, 10 minutes, 9 minutes, 8 minutes, 7 minutes, 6 minutes, 5 minutes, 4 minutes, 3 minutes, 2 minutes or 1 minute.

The incubation in step (ii) or the isolation of nucleic acids from the samples may be for at least 10 seconds, at least 30 seconds, at least 1 minutes, at least 2 minutes, at least 3 minutes, at least 4 minutes, at least 5 minutes, at least 7 minutes, at least 10 minutes, at least 30 minutes and/or at most 1 hour or wherein the isolating of nucleic acids from a sample is at a temperature of at least 40° C. for at least 10 seconds, at least 30 seconds, at least 1 minute, at least 2 minutes, at least 3 minutes, at least 4 minutes, at least 5 minutes, at least 7 minutes, at least 10 minutes, at least 30 minutes.

It is thus also envisioned that the solution including the sample is incubated at a temperature of at least about 60° C. for at least 10 seconds or the isolating of nucleic acids from a sample is at a temperature of at least about 60° C. for at least 10 seconds. It is further contemplated that the solution including the sample has a temperature of at least about 60° C., preferably for at least 10 seconds.

It is also envisioned that the solution including the sample is incubated at a temperature of at least about 60° C. for at least 10 minutes, at least 15 minutes or at least 30 minutes or wherein the isolation of nucleic acids from a sample is at a temperature of at least about 60° C. for at least 10 minutes, at least 15 minutes or at least 30 minutes and optionally at most for one hour.

It is also envisioned that the solution including the sample is incubated at a temperature of at least about 60° C. for 10-60 minutes, 15-60 minutes, 15-40 minutes or at least about 60° C. for 10-60 minutes, 15-60 minutes, 15-40 minutes or 15-30 minutes.

It is also envisioned that the solution including the sample is incubated at a temperature of at least about 60° C. for at least 10 seconds, for at least 30 seconds, or for at least 1 minute, 5 minutes, 10 minutes, 15 minutes or more or for at least 10 seconds to 1 hour, preferably 10 seconds to 40 minutes, more preferably 1 minute to 30 minutes, most preferably between 1 minute and 20 minutes or the isolating of nucleic acids from a sample is at a temperature of at least about 60° C. at least 10 seconds, for at least 30 seconds, or for at least 1 minute, 5 minutes, 10 minutes, 15 minutes or more or for at least 10 seconds to 1 hour, preferably 10 seconds to 40 minutes, more preferably 1 minute to 30 minutes, most preferably between 1 minute and 10 minutes, wherein the solution optionally comprises about 1 mM to 500 mM, preferably 5 mM to 500 mM reducing agent, more preferably 5 mM to 100 mM reducing agent, most preferably 10 mM to 40 mM reducing agent and/or optionally has a pH of about 2-13, preferably about 4-11 or about 4-10, more preferably about 6-9.

It is further contemplated that the solution including the sample has a temperature of at least about 60° C. at least 10 seconds, for at least 30 seconds, or for at least 1 minute, 5 minutes, 10 minutes, 15 minutes or more or for at least 10 seconds to 1 hour, preferably 10 seconds to 40 minutes, more preferably 1 minute to 30 minutes, most preferably between 1 minute and 10 minutes, wherein the solution optionally comprises about 1 mM to 500 mM, preferably 5 mM to 500 mM reducing agent, more preferably 5 mM to 100 mM reducing agent, most preferably 10 mM to 40 mM reducing agent and/or optionally has a pH of about 2-13, preferably about 4-11 or about 4-10, more preferably about 6-9.

It is also envisioned that the solution including the sample is incubated at a temperature of at least about 70° C. for at least 10 seconds, for at least 30 seconds, or for at least 1 minute, 5 minutes, 10 minutes, 15 minutes or more or for at least 10 seconds to 1 hour, preferably 10 seconds to 40 minutes, more preferably 1 minute to 30 minutes, most preferably between 1 minute and 10 minutes or the isolating of nucleic acids from a sample is at a temperature of at least about 70° C. at least 10 seconds, for at least 30 seconds, or for at least 1 minute, 5 minutes, 10 minutes, 15 minutes or more or for at least 10 seconds to 1 hour, preferably 10 seconds to 40 minutes, more preferably 1 minute to 30 minutes, most preferably between 1 minute and 10 minutes, wherein the solution optionally comprises about 1 mM to 500 mM, preferably 5 mM to 500 mM reducing agent, more preferably 5 mM to 100 mM reducing agent, most preferably 10 mM to 40 mM reducing agent and/or optionally has a pH of about 2-13, preferably about 4-11 or about 4-10, more preferably about 6-9.

It is further contemplated that the solution including the sample has a temperature of at least about 70° C. at least 10 seconds, for at least 30 seconds, or for at least 1 minute, 5 minutes, 10 minutes, 15 minutes or more or for at least 10 seconds to 1 hour, preferably 10 seconds to 40 minutes, more preferably 1 minute to 30 minutes, most preferably between 1 minute and 10 minutes, wherein the solution optionally comprises about 1 mM to 500 mM, preferably 5 mM to 500 mM reducing agent, more preferably 5 mM to 100 mM reducing agent, most preferably 10 mM to 40 mM reducing agent and/or optionally has a pH of about 2-13, preferably about 4-11 or about 4-10, more preferably about 6-9.

It is also envisioned that the solution including the sample is incubated at a temperature of at least about 75° C., 80° C. or 85° C. for at least 10 seconds, for at least 30 seconds, or for at least 1 minute, 2 minutes, 3 minutes, 4 minutes, 5 minutes or more or for at least 10 seconds to 1 hour, preferably 10 seconds to 10 minutes, more preferably 1 minute to 10 minutes, most preferably between 3 minutes and 5 minutes or the isolating of nucleic acids from a sample is at a temperature of at least about 75° C., 80° C. or 85° C. at least 10 seconds, for at least 30 seconds, or for at least 1 minute, 2 minutes, 3 minutes, 4 minutes, 5 minutes or more or for at least 10 seconds to 1 hour, preferably 10 seconds to 10 minutes, more preferably 1 minute to 10 minutes, most preferably between 3 minutes and 5 minutes, wherein the solution optionally comprises about 1 mM to 500 mM, preferably 5 mM to 500 mM reducing agent, more preferably 5 mM to 100 mM reducing agent, most preferably 10 mM to 40 mM reducing agent and/or optionally has a pH of about 2-13, preferably about 4-11 or about 4-10, more preferably about 6-9.

It is further contemplated that the solution including the sample has a temperature of at least about 75° C., 80° C. or 85° C. at least 10 seconds, for at least 30 seconds, or for at least 1 minute, 2 minutes, 3 minutes, 4 minutes, 5 minutes or more or for at least 10 seconds to 1 hour, preferably 10 seconds to 10 minutes, more preferably 1 minute to 10 minutes, most preferably between 3 minutes and 5 minutes, wherein the solution optionally comprises about 1 mM to 500 mM, preferably 5 mM to 500 mM reducing agent, more preferably 5 mM to 100 mM reducing agent, most preferably 10 mM to 40 mM reducing agent and/or optionally has a pH of about 2-13, preferably about 4-11 or about 4-10, more preferably about 6-9.

Additionally or alternatively, the solution including the sample is incubated at a temperature of about 60° C. to about 95° C. for 1 minute to 30 minutes or the isolating of nucleic acids from a sample is at a temperature about 60° C. to about 95° C. for 1 minute to 10 minutes. It is further contemplated that the solution including the sample is incubated at a temperature of about 60° C. to about 95° C. for 1 minute to 10 minutes.

It is also envisioned that the solution including the sample is incubated at a temperature of about 60° C. to about 95° C. for 1 minute to 30 minutes or the isolating of nucleic acids from a sample is at a temperature of about 60° C. to about 95° C. for 1 minute to 10 minutes, wherein the solution optionally comprises about 5-100 mM reducing agent and/or has a pH of about 4-11. It is further contemplated that the solution including the sample is incubated at a temperature of about 60° C. to about 95° C. for 1 minute to 10 minutes, wherein the solution optionally comprises about 5-100 mM reducing agent and/or has a pH of about 4-11 or about 4-10, more preferably about 6-9.

Additionally or alternatively, the solution including the sample is incubated at a temperature of about 75° C. to about 85° C., preferably about 80° C. to about 85° C. for about 3-5 minutes or the isolating of nucleic acids from a sample is at a temperature of about 75° C. to about 85° C. for about 3-5 minutes. It is further contemplated that the solution including the sample is incubated at a temperature of about 75° C. to about 85° C., preferably about 80° C. to about 85° C. for about 3-5 minutes.

It is also envisioned that the solution including the sample is incubated at a temperature of about 75° C. to about 85° C., preferably about 80° C. to about 85° C. for about 3-5 minutes or the isolating of nucleic acids from a sample is at a temperature of about 75° C. to about 85° C., preferably about 80° C. to about 85° C. for about 3-5 minutes, wherein the solution optionally comprises about 5-100 mM, preferably 10-40 mM reducing agent and has a pH of about 4-11, preferably of about 5-8. It is further contemplated that the solution including the sample is incubated at a temperature of about 75° C. to about 85° C. for about 3-5 minutes, wherein the solution optionally comprises about 5-100 mM, preferably 10-40 mM reducing agent and has a pH of about 4-11 or about 4-10, more preferably about 6-9, or of about 5-8.

The skilled person knows how solutions can be incubated at a certain temperature. Further, it is clear that in laboratories standard containers such as Eppendorf tubes etc. are used. It is expected that these standard tubes as well as solutions therein instantly heat up to the desired temperature e.g. when temperature/heat is applied via a thermal shaker.

It is preferred, that the thermal shaker shakes with at least 800 rpm, more preferably 1400 rpm.

Principally the skilled in the art understands that the temperature, the time the temperature is applied/present and/or the amount of the reducing agent may be interrelated factors as also described in the Examples. As such, the higher the temperature, the less can be the time the temperature can be applied and/or the concentration of the reducing agent.

The incubation or the isolation of sample take place at different temperatures as disclosed herein. In principle, the temperature can be achieved in different ways.

On the one hand, the solution as well as the sample can be prepared at a temperature of e.g. 60° C. or any other temperature as indicated herein and then contacted with each other. Afterwards, the solution including the sample is introduced into a thermal shaker that has been pre-warmed to the same temperature for a certain period of time.

On the other hand, the solution as well as the sample can be prepared at room temperature of about 20° C. and then contacted with each other. Afterwards, the solution including the sample can be introduced into a thermal shaker that has been pre-warmed to the temperature of e.g. 60° C. or any other temperature as indicated herein for a certain period of time.

A further option is that the solution as well as the sample are prepared at a temperature of about 90° C. and then contacted with each other. The solution including the sample is then left at room temperature e.g. at 20° C. until it reaches the temperature of interest such as 60° C. or any other temperature as disclosed herein.

It is further envisioned that the methods/uses may additionally or alternatively comprise the step of (i01) mechanical homogenizing of the sample. The skilled person knows ways how to mechanically homogenize a sample some of which are inter alia described by Burden (2008) "Guide to the Homogenization of Biological Samples" Random Primers, Issue No. 7, September 2008, page 1-14. In general, the mechanical homogenization means the disruption of the sample. For example, the sample may be mechanically homogenized by grinding, shearing, beating, shock or combinations thereof.

Grinding may be accomplished by contacting the sample with a grain mill, coffee grinder, vortexer, bead beater or glass homogenizer. Grinding relies on creating friction by sandwiching the sample between two hard surfaces that slide against each other.

Shearing may be accomplished by contacting the sample with blender or rotor-stator. Upon shearing a tangential force is being applied to the sample.

Beating relates to beating a sample using a projectile. Most bead beating methods rely on placing a sample and beads in a tube and rapidly shaking them back and forth. For example, the mechanical homogenizing of the sample may be achieved by beadbeating such a dry beadbeating or wet beadbeating.

Shock (pressure) includes inter alia shock waves used for disrupting samples as e.g. with ultrasonication.

It is envisioned that the step of mechanical homogenizing of the sample takes place before contacting the sample in step (i).

The present methods/uses may additionally or alternatively include a step of contacting the sample with an enzyme. This enzyme digestion step can, for example, take place either before step (i), namely before contacting the sample herein or after step (i).

Therefore, the methods/uses may further comprises step (i02) contacting the sample with an enzyme before contacting the sample in step (i). It is however also envisioned that the method further comprises step (i1) contacting the (lysis) sample obtained in step (i) with an enzyme.

Steps (i02) and (i1) typically require incubation at a temperature of about 60° C. Thus, step (a02) and (a1) can be performed at about 60° C. The enzyme may be deactivated by raising the temperature to about 80° C. or even 90° C. In cases where the step (i02) is performed before step (i) the heating (incubation at 40° C. or more) of the solution contacted with the sample will inactivate the enzyme. In cases where step (i1) is performed after step (i), the methods may include an additional incubation step (up to 80° C. or 90° C.).

The present methods/uses may additionally or alternatively comprise a step (iii) contacting the solution including the sample with a clearing solution (h).

It is further preferred that the solution as described herein, particularly the solution of the invention, additionally comprises a clearing solution (h).

The clearing solution has the effect that the anionic detergent can be precipitated. Thus, the clearing solution is typically added in a method in which the sample has been contacted with an anionic detergent e.g. within the (lysis) solution.

Thus, where the suitable detergent is an anionic detergent, the clearing solution may comprise a cationic ion for the precipitation of said detergent. Suitable cationic ions may include e.g. $K^+$, $Rb^+$, $Cs^+$, $Mg^{++}$, $Ca^{++}$, $Sr^{++}$ or $Ba^{++}$. In some embodiments, the cation may be $K^+$, $Rb^+$ or $Cs^+$. Preferably, the cation may be $Mg^{++}$, $Ca^{++}$, $Sr^{++}$ or $Ba^{++}$. More preferably, the cation may be $Ca^{++}$, $Sr^{++}$ or $Ba^{++}$. Still more preferably, the cationic ion may be $Ca^{++}$ or $Sr^{++}$. Even more preferably, the cation is $Sr^{++}$. It is also envisioned that the cationic ion is Al, Zn, Sn or Fe. Preferably, in any one of these embodiments, the anionic detergent is sodium dodecyl sulfate (SDS), lithium dodecyl sulfate (LiDS), ammonium dodecyl sulfate, monoethanolamine dodecyl sulfate, diethanolamine dodecyl sulfate, or triethanolamine dodecyl sulfate. More preferably, the anionic detergent is sodium dodecyl sulfate (SDS), lithium dodecyl sulfate (LiDS), ammonium dodecyl sulfate, monoethanolamine dodecyl sulfate, or triethanolamine dodecyl sulfate. Still more preferably, the anionic detergent is sodium dodecyl sulfate (SDS), lithium dodecyl sulfate (LiDS), or ammonium dodecyl sulfate. Still more preferably, the anionic detergent is sodium dodecyl sulfate (SDS) or lithium dodecyl sulfate (LiDS). Even more preferably, the anionic detergent is sodium dodecyl sulfate (SDS).

The clearing solution may thus comprise KCl, KBr, Kl, RbCl, RbBr, Rbl, CsCl, CsBr, Csl, $MgCl_2$, $MgBr_2$, $Mgl_2$, $CaCl_2$, $CaBr_2$, $Cal_2$, $SrCl_2$, $SrBr_2$, $Srl_2$, $BaCl_2$, $BaBr_2$, or $Bal_2$. In some embodiments, the clearing solution may comprise KCl, KBr, Kl, RbCl, RbBr, Rbl, CsCl, CsBr or Csl. In some embodiments, the clearing solution may comprise KCl, KBr, Kl, RbCl, RbBr, or Rbl. Preferably, the clearing solution may comprise $MgCl_2$, $MgBr_2$, $Mgl_2$, $CaCl_2$, $CaBr_2$, $Cal_2$, $SrCl_2$, $SrBr_2$, $Srl_2$, $BaCl_2$, $BaBr_2$, or $Bal_2$. More preferably, the clearing solution may comprise $CaCl_2$, $CaBr_2$, $Cal_2$, $SrCl_2$, $SrBr_2$, $Srl_2$, $BaCl_2$, $BaBr_2$ or $Bal_2$. Still more preferably, the clearing solution may comprise $CaCl_2$ or $SrCl_2$. Even more preferably, the clearing solution may comprise $SrCl_2$.

For example, the clearing solution may comprise 6 M, 5 M, 4 M, 3 M, 2 M, 1 M, 0.5 M, 0.25 M or less of a salt comprising $K^+$, $Rb^+$, $Cs^+$, $Mg^{++}$, $Ca^{++}$, $Sr^+$ or $Ba^{++}$. In some embodiments, the clearing solution may comprise 6 M, 5 M, 4 M, 3 M, 2 M, 1 M, 0.5 M, 0.25 M or less of a salt comprising $K^+$, $Rb^+$ or $Cs^+$. Preferably, the clearing solution may comprise 6 M, 5 M, 4 M, 3 M, 2 M, 1 M, 0.5 M, 0.25 M or less of a salt comprising $Mg^{++}$, $Ca^{++}$, $Sr^{++}$ or $Ba^{++}$. More preferably, the clearing solution may comprise 6 M, 5 M, 4 M, 3 M, 2 M, 1 M, 0.5 M, 0.25 M or less of a salt comprising $Ca^{++}$, $Sr^{++}$ or $Ba^{++}$. Still more preferably, the clearing solution may comprise 6 M, 5 M, 4 M, 3 M, 2 M, 1 M, 0.5 M, 0.25 M or less of a salt comprising $Ca^{++}$ or $Sr^{++}$. Even more preferably, the clearing solution may comprise 6 M, 5 M, 4 M, 3 M, 2 M, 1 M, 0.5 M, 0.25 M or less of a salt comprising Sr**.

The clearing solution may comprise 6 M, 5 M, 4 M, 3 M, 2 M, 1 M, 0.5 M, 0.25 M or less of KCl, KBr, Kl, RbCl, RbBr, Rbl, CsCl, CsBr, Csl, $MgCl_2$, $MgBr_2$, $Mgl_2$, $CaCl_2$, $CaBr_2$, $Cal_2$, $SrCl_2$, $SrBr_2$, $Srl_2$, $BaCl_2$, $BaBr_2$, or $Bal_2$. In some embodiments, the clearing solution may comprise 6 M, 5 M, 4 M, 3 M, 2 M, 1 M, 0.5 M, 0.25 M or less of KCl, KBr, Kl, RbCl, RbBr, Rbl, CsCl, CsBr or Csl. In some embodiments, the clearing solution may comprise 6 M, 5 M, 4 M, 3 M, 2 M, 1 M, 0.5 M, 0.25 M or less of KCl, KBr, Kl, RbCl, RbBr, or Rbl. Preferably, the clearing solution may comprise 6 M, 5 M, 4 M, 3 M, 2 M, 1 M, 0.5 M, 0.25 M or less of $MgCl_2$, $MgBr_2$, $Mgl_2$, $CaCl_2$, $CaBr_2$, $Cal_2$, $SrCl_2$, $SrBr_2$, $Srl_2$, $BaCl_2$, $BaBr_2$, or $Bal_2$. More preferably, the clearing solution may comprise 6 M, 5 M, 4 M, 3 M, 2 M, 1 M, 0.5 M, 0.25 M or less of $CaCl_2$, $CaBr_2$, $Cal_2$, $SrCl_2$, $SrBr_2$, $Srl_2$, $BaCl_2$, $BaBr_2$, or $Bal_2$. Still more preferably, the clearing solution may comprise 6 M, 5 M, 4 M, 3 M, 2 M, 1 M, 0.5 M, 0.25 M or less of $CaCl_2$ or $SrCl_2$. Even more preferably, the clearing solution may comprise 6 M, 5 M, 4 M, 3 M, 2 M, 1 M, 0.5 M, 0.25 M or less of $SrCl_2$. Thus, the clearing solution may comprise 1 or 2 M $SrCl_2$. The clearing solution may comprise 1 or 2 M $SrCl_2$ in aqua dest. or in 20 mM Tris HCl at pH 8.

The present methods/uses can additionally or alternatively include a step (iii) namely, separating the non-nucleic acid compounds from the nucleic acids. The person skilled knows what non-nucleic acid compounds can be.

For example, the non-nucleic acid components are all non-nucleic acid compounds in the solution obtained in step (i), (i1), (ii) or (ii1). Non-nucleic acid components may for example be proteins, salts, chaotropic salts, detergents, organic or inorganic solvents, dyes, metabolites, sample debris, low molecular molecules, preferably nucleotides and/or PCR inhibitors. Non-nucleic acid components thus include proteins, salts, chaotropic salts, detergents, organic or inorganic solvents, dyes, metabolites and nucleotides.

For example, the separation may include precipitating nucleic acids. Such precipitation may include binding to nucleic acids.

For example, solid phase components (also called solid phases) that are capable of binding to nucleic acids under suitable conditions may be used to precipitate nucleic acids. Exemplary solid phase components include silica particles, silcon dioxide, diatomateous earth, glass, alkyl-silica, aluminium silicate, borosilicate, nitrocellulose, diazotized paper, nylon, metal oxides, zirconia, alumina, hydrophobic chromatography resins.

Thus, step (iii) separating the non-nucleic acid compounds from the nucleic acids may comprise the use of solid phase components capable of binding to nucleic acids. Yet, in some embodiments nucleic acids are isolated without the use of solid phase components that is capable of binding to nucleic acids as described herein.

Also, certain polymers are capable of precipitating nucleic acids. Thus, step (iii) separating the non-nucleic acid compounds from the nucleic acids may comprise the use of polymers capable of binding to nucleic acids. Examples of such polymers are polyethyleneeimine, DEAE dextran, polylysine, polyarginine, polyhistidine. Yet, in some embodiments nucleic acids are isolated without the use of polymers as described herein.

Also, certain alcohols are capable of precipitating nucleic acids. Exemplary alcohols include ethanol, propanol, or butanol. Thus, step (iii) separating the non-nucleic acid compounds from the nucleic acids may comprise the use of alcohols. However, it is also envisioned that the methods described herein do not comprise a step of contacting the lysis sample of step (a) with an alcohol.

It is further contemplated that step (iii) separating the non-nucleic acid compounds from the nucleic acids may comprise isolation of nucleic acids from aqueous solution. Such isolation of nucleic acids can include by contacting the solution including the sample of step (i), (i1), (ii) or (iii) with an organic solvent. Examples of organic solvents may include phenol, combinations of phenol and chloroform and the like.

It is envisioned that the separating may include a transfer of the product/sample/solution including the sample of step (i), (i1), (ii) or (ii1) onto a matrix capable of retaining non-nucleic acid components, while the nucleic acids pass through the matrix. Such matrices can, for example, be any gel filtration matrix (gel filtration chromatography matrix). For example, the matrix may be a sephacryl resin or a matrix comprising hydroxylated methacrylic polymers. Exemplary sephacryl resins are Sephacryl S100, Sephacryl S200, Sephacryl S300, Sephacryl S400 or Sephacryl S500, preferably Sephacryl S400. It is thus envisioned that the matrix is a Sephacryl resin. Exemplary matrices comprising hydroxylated methacrylic polymers are matrices comprising methacrylate (ethylene glycol/methacrylate copolymer(s)). For example, such matrix maybe a HW-40, HW-50, HW-55, HW-65 or HW-70 matrix. It is also envisioned that the matrix is a HW65S. Such HW-matrices are inter alia obtainable from Tosoh Haas. It is also envisaged that the matrix is a silica membrane or an ion exchange resin. Yet, in some embodiments nucleic acids are isolated without the use of a matrix.

The present invention also relates to a kit comprising the solution of the invention (a) and optionally the clearing solution as described herein. The kit may further comprise (b) means for enzymatic digestion; and/or (c) means such as a matrix for separating of non-nucleic acid components from nucleic acids, preferably a resin for separating of non-nucleic acid components from nucleic acids.

The solution of the invention as disclosed herein may be a lysis solution.

It is also contemplated for the methods, uses, kits and solutions described herein above that the reducing agent is a compound according to formula (II):

(II)

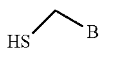

wherein B is selected from the group consisting of

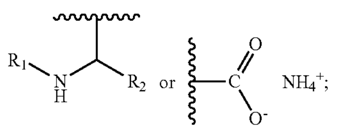

wherein $R_1$ is selected from the group consisting of

—H, —C(=O)($C_1$-$C_{15}$)alkyl, and —C(=O)$(CH_2)_{n1}$C(H)(N($R_3$)$R_4$)$COOR_5$, n1 is 1-15, $R_2$ is selected from the group consisting of —H, —C(=O)NH$(CH_2)_{n2}$$COOR_6$, —($C_1$-$C_{15}$)alkyl, —$OR_7$, —COORs, and —N($R_9$)$R_{10}$, $n_2$ is 1-15, $R_3$ to $R_{10}$ are independently selected from the group consisting of —H, and —($C_1$-$C_{15}$)alkyl, and a salt, complex, racemic mixture, diastereomer, enantiomer, tautomer, or isotopically enriched form thereof.

It goes without saying that this reducing agent (b) according to formula (II) may be employed in all embodiments of the present invention. Thus, in some embodiments, the reducing agent (b) according to formula (II) may be used in addition to the reducing agent of formula (I). Alternatively, the reducing agent (b) according to formula (II) may be used instead of the reducing agent of formula (I) (in other words, the reducing agent (b) according to formula (II) may replace the reducing agent of formula (I)).

Thus, in one embodiment, the method as described herein may also include the step of contacting the sample with a lysis solution to obtain a lysis sample comprising inter alia a reducing agent of the formula (II) as defined herein. Generally, any suitable reducing agent being of formula (11) can be used in the lysis solution as described herein. The skilled person knows suitable reducing agents having formula (II).

It is preferred that in formula (II)

i) $R_2$ is selected from the group consisting of H, —C(=O)NH$(CH_2)_{n2}$$COOR_6$, —($C_1$-$C_{15}$)alkyl, —$OR_7$, and —$COOR_8$, preferably H, and —C(=O)NH$(CH_2)_{n2}$$COOR_6$ and/or ii) $R_3$ to $R_{10}$ are independently selected from the group consisting of —H, and/or iii) $n_1$ is 1-5, preferably 2 and/or iv) $n_2$ is 1-5, preferably 1.

It is more preferred that the reducing agent according to formula (11) is selected from the group consisting of cystein, glutathione, ammonium thioglycolate and N-acetylcysteamine.

Thus, in another embodiment, the methods/uses as described herein include the step of contacting the sample with a solution comprising inter alia a reducing agent of the formula (II) as defined herein.

It is also contemplated for the methods, uses and solutions described herein above that the reducing agent is in one embodiment a compound that provides $SO_3^{2-}$ ions or $S_2O_4^{2+}$ in solution. It goes without saying that this reducing agent may be employed in all embodiments of the present invention. Thus, in some embodiments, the compound that provides $SO_3^{2-}$ ions or $S_2O_4^{2-}$ in solution may be used in addition to the reducing agent of formula (I). Alternatively, the compound that provides $SO_3^{2-}$ ions or $S_2O_4^{2+}$ in solution may be used instead of the reducing agent of formula (I) (in other words, the compound that provides $SO_3^{2-}$ ions or $S_2O_4^{2-}$ in solution may replace the reducing agent of formula (I)). $SO_3^{2-}$ is the sulfite anion.

$S_2O_4^{2-}$ is the dithionite anion.

Thus, in one embodiment, the method as described herein may also include the step of contacting the sample with a lysis solution to obtain a lysis sample comprising inter alia as reducing agent a compound that provides $SO_3^{2-}$ ions or $S_2O_4^{2-}$ in solution.

Generally, any suitable reducing agent that provides $SO_3^{2-}$ ions or $S_2O_4^{2-}$ in solution can be used in the lysis solution as described herein. The skilled person knows suitable reducing agents that provide for $SO_3^{2-}$ ions or $S_2O_4^{2-}$ in solution.

It is preferred that the agent providing $SO_3^{2-}$ ions in solution, also comprises hydrogen sulfites. Hydrogen sulfites are preferably selected from the group consisting of $Na_2SO_3$, $KHSO_3$, $NaHSO_3$, $K_2SO_3$, $ZnSO_3$, $CuSO_3$, $CdSO_3$, $SrSO_3$, $MgSO_3$, $CaSO_3$, $BaSO_3$; $PbSO_3$; more preferably $Na_2SO_3$, $NaHSO_3$ $K_2SO_3$, $ZnSO_3$, $MgSO_3$, $CaSO_3$ and/or the agent providing $S_2O_4^{2-}$ ions in solution is preferably selected from the group consisting of $Na_2S_2O_4$, $K_2S_2O_4$, $ZnS_2O_4$, $CuS_2O_4$, $CdS_2O_4$, $CaS_2O_4$, $SrS_2O_4$, $BaS_2O_4$, $PbS_2O_4$, $MgS_2O_4$; more preferably $Na_2S_2O_4$, $K_2S_2O_4$, $ZnS_2O_4$, $CaS_2O_4$, $MgS_2O_4$.

It is more preferred that the reducing agent is selected from the group consisting of sodium hydrogen sulfite, sodium hydrosulfite or sodium sulfite.

It is noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no at least routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "less than" or in turn "at least" does not include the concrete number.

For example, less than 20 means less than the number indicated. Similarly, at least or greater than means at least or greater than the indicated number, e.g. at least 80% means at least or greater than the indicated number of 80%.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". When used herein "consisting of" excludes any element, step, or ingredient not specified.

The term "including" means "including but not limited to". "Including" and "including but not limited to" are used interchangeably.

When used herein, the term "about" is understood to mean that there can be variation in the respective value or range (such as pH, concentration, percentage, molarity, number of amino acids, time etc.) that can be up to 5%, up to 10% of the given value. For example, if a formulation comprises about 5 mg/ml of a compound, this is understood to mean that a formulation can have between 4.5 and 5.5 mg/ml.

It should be understood that this invention is not limited to the particular methodology, protocols, material, reagents, and substances, etc., described herein and as such can vary. The terminology used herein is for the purpose of describing particular embodiments only and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The content of all documents and patent documents cited herein is incorporated by reference in their entirety.

A better understanding of the present invention and of its advantages will be had from the following examples, offered for illustrative purposes only. The examples are not intended to limit the scope of the present invention in any way.

EXAMPLES OF THE INVENTION

Example 1: Lysis Using Different TCEP Concentrations Compared to a Standard Protocol CHO cells obtained from the Fraunhofer Institute were lysed using two different lysis protocols.

On the one hand, $10^6$ CHO cells were lysed using a lysis solution (lysis solution LS) of the following components: 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O_8$*2 $H_2O$), 50 mM ammonium chloride. The pH of this buffer was set at pH 8 by the addition of NaOH.

In this experimental set up, the lysis included the following steps:

1. Harvesting cells by centrifugation at 2000×g in a 1.5 ml reaction tube and remove supernatant.
2. Adding 55 μl of the lysis solution LS and 25 μl of protease and resuspend cell pellet completely by pulse-vortexing (pH=10).
3. Place reaction tube in the thermal shaker and incubate at 60° C. for 10 minutes with max. agitation.
4. Add 10 μl of clearing solution (2 M $SrCl_2$ in 20 mM Tris and further addition of 20.165 ml/L of 15% HCl) and 1 μl of RNase to each lysed sample and vortex vigorously with four pulses of 10 seconds each. The samples become cloudy.
5. Incubate for 2 minutes at room temperature to remove RNA.
6. Centrifuge for 2 minutes at maximal speed.
7. Transfer lysis supernatant (max. 100 μl) containing the DNA onto a spin column. The column includes a filter/resin made of Resin Sephacryl S400. This resin filters residues of salts, peptides, solids e.g. colors, unprecipitated SDS or solubilized SDS residues.
8. Centrifuge for 1 min at 1000× g. The supernatant is pressed through the column by centrifuging for 1 minute at 1000× g. The purified genomic DNA elutes into the 1.5 ml elution tube and can be immediately applied in downstream applications.

On the other hand, pelleted $10^6$ CHO cells were resuspended and lysed using 80 μl lysis solution (lysis buffer) of the following components: 10 mM, 20 mM, 30 mM, 40 mM or 50 mM TCEP, 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O_8$*2 $H_2O$) and 50 mM ammonium chloride. The ammonium chloride increases the solubility of the DNA and thus also the DNA yield. The pH of this buffer was set at 7 by the addition of NaOH/HCl. The lysis was performed for 3 minutes at 80° C. in a 1.5 ml safe-lock Eppendorf tube in a thermal shaker that was pre-warmed at 80° C. before the tubes were introduced into the thermal shaker. The incubation was performed at 1400 rpm. Importantly, this experimental setup did not include the use of an enzyme digestion step.

Afterwards the lysed cells were contacted with 15 μl of clearing solution (2 M $SrCl_2$ in 20 mM Tris and further addition of 20.165 ml/L of 15% HCl). The addition of the clearing solution has the effect that anionic detergents are precipitated. Then the samples were centrifuged, and the supernatant was passed over a column. The column includes a filter/resin made of Resin Sephacryl S400. The supernatant is pressed through the column by centrifuging for 1 minute at 1000× g.

DNA/RNA (nucleic acid) concentration can be assessed by different methods. In the following absorbance (optical density) and agarose gel electrophoresis measurements are described as indicators for the obtained quality of the obtained nucleic acids.

Firstly, the obtained nucleic acids were analyzed by photometric measurements. Here, the principle is that nucleic acids absorb ultraviolet (UV) light due to the heterocyclic rings of the nucleotides, while the sugar-phosphate backbone does not contribute to absorption. The wavelength of maximum absorption for both DNA and RNA is 260 nm (λmax=260 nm) with a characteristic value for each base. The absorption properties of DNA can be used for detection, quantification and assessment of purity. Although the Amax is constant, the extinction coefficient of nucleic acids depends on their environment.

In below Table 1 two different measurements have been performed, namely a single measurement of the absorbance at a wavelength of 260 nm (A260; 7$^{th}$ column), a single measurement of the absorbance at a wavelength of 280 nm (A260; 8th column). Furthermore, the ratio of the absorbance detected at a wavelength of 260 nm and 280 nm (ratio of A260/A280) and the ratio of an absorbance detected at a wavelength of 260 nm and 230 nm (ratio of A260/A230) are depicted.

Generally, the absorbance at 260 nm is used to calculate the concentration of nucleic acids. At a concentration of 50 μg/ml and a 1 cm path length* dsDNA has A260 nm=1. The absorbance value is also dependent on the amount of secondary structure in the DNA due to hypochromicity. For reliable spectrophotometric DNA quantification A260 readings should lie between 0.1 and 1.0.

The purity of DNA can be detected by the A260/A280 ratio. This is because this ratio gives an indication of protein contamination. However, the A260/A280 ratio is only an indication of purity rather than a precise answer. Pure DNA preparations have an A260/A280 ratio of greater than or equal to 1.8. Pure RNA has an A260/A280 ratio of 2.0, therefore if a DNA sample has an A260/A280 ratio of greater than 1.8 this could suggest presence of RNA.

The A260/A230 ratio is a secondary measure of nucleic acid purity. The A260/A230 ratio values for pure samples are often higher than the respective A260/A280 ratio values. Strong absorbance around 230 nm can indicate that organic compounds or chaotropic salts are present in the purified nucleic acids. A ratio of 260 nm to 230 nm can help evaluate the level of salt carryover in the purified nucleic acids. The lower the ratio, the greater the amount of salt present. As a guideline, the A260/A230 ratio should be greater than 1.5, ideally close to 1.8.

The results of these measurements are depicted in below Table.

TABLE 1

Results obtained for spectrophotometric nucleic acid quantification of the different samples.

| sample | Type of sample | protocol | Nucleic acid sequences (ng/μL) | A260/ A280 | A260/ A230 | A260 | A280 |
|---|---|---|---|---|---|---|---|
| 1 | CHO | standard protocol | 66.587 | 1.833 | 2.156 | 1.332 | 0.727 |
| 2 | CHO | standard protocol | 74.483 | 1.74 | 1.944 | 1.49 | 0.856 |
| 3 | CHO | 50 mM TCEP, 3 Min, 80° C. | 92.883 | 1.829 | 1.543 | 1.858 | 1.016 |
| 4 | CHO | 40 mM TCEP, 3 Min, 80° C. | 66.386 | 1.707 | 1.632 | 1.328 | 0.778 |
| 5 | CHO | 30 mM TCEP, 3 Min, 80° C. | 81.311 | 1.794 | 1.69 | 1.626 | 0.907 |
| 6 | CHO | 20 mM TCEP, 3 Min, 80° C. | 72.392 | 1.669 | 1.557 | 1.448 | 0.867 |
| 7 | CHO | 10 mM TCEP, 3 Min, 80° C. | 38.378 | 1.719 | 1.53 | 0.768 | 0.446 |

As can be obtained from Table 1, the spectrophotometric nucleic acid quantification of A260 readings (7$^{th}$ column in Table 1) all lay between 0.1 and 1.0. Thus, these measurements are reliable. This measurement was used for the determination of the final concentration of the obtained nucleic acids as depicted in the 4$^{th}$ column of Table 1.

Furthermore, as shown by the ratio of A260/A280, all samples provide for a ratio close to 1.8. Since pure DNA preparations have an A260/A280 ratio of greater than or equal to 1.8 it is assumed that none of the samples 1-7 includes relevant amounts of additional RNA.

To determine the purity of nucleic acids obtained by the different lysis the A260/A230 ratio was determined (6$^{th}$ column in Table 1). As shown in above Table 1 the A260/A230 ratio was greater than 1.5 for all samples. This indicates that the nucleic acids were of good purity and that non-nucleic acid components were present only in low amounts—if at all.

More specifically, Table 1 shows that both the standard protocol as well as the lysis with TCEP results in non-degraded DNA at a sufficient amount. Lowest amounts of nucleic acids were obtained using a lysis buffer with TCEP at a concentration of 10 mM. Yet, TCEP concentrations of 20 mM, 30 mM, 40 mM and 50 mM provided for comparable DNA amounts. Lysis with TCEP concentrations of 50 mM and 30 mM (92.883 ng/μL nucleic acids and 81.311 ng/μL nucleic acids) even resulted in higher nucleic acid amounts than the amount of nucleic acids obtained when using the standard protocol (66.587 ng/μL nucleic acids and 74.483 ng/μL nucleic acids).

The photometric measurements proof that by the different tested lysis protocols nucleic acids can be obtained with high purity and in sufficient amounts to allow for further analysis.

Further, the obtained nucleic acids were analyzed by gel electrophoresis. In order to visualize the nucleic acids in the agarose gel, staining with an intercalating dye such as ethidium bromide or SYBR Green is required. One reason for running a gel is to access nucleic acid quality. On a 1 to 1.5% agarose gel, intact genomic DNA should appear as a compact, high-molecular-weight band with no low-molecular-weight smears. Degraded DNA results in biased labelling.

The gel electrophoresis performed with the different samples used in this experiment are depicted in FIG. 1. In the here described experiments, a 0.8% agarose gel and the dye GelRed has been used. The gel in FIG. 1A reflects nucleic acids obtained by sample 1 and 2. The gel depicted in FIG. 1B shows nucleic acids obtained by sample 3, 4, 5, 6, and 7.

As evident from FIG. 1, all samples provide for a high-molecular-weight band with no low-molecular-weight smears indicating that only low or no amounts of degraded nucleic acids are present in the tested samples.

Example 2: Lysis Using TCEP at Different pH

To determine the influence of the pH on the lysis using TCEP, the following experiment has been performed. 200 µl whole blood as sample was washed once with an erythrocyte lysis buffer (10 mM sodium hydrate carbonate ($NaHCO_3$), 155 mM ammonium chloride, 0.1 mM $Na_2EDTA$, pH 7.3). For this washing 1.3 ml of the erythrocyte lysis buffer were added to the sample. The incubation was performed for 3 minutes at room temperature of about 20° C. Afterwards, the sample was centrifuged for 2 minutes at 2000 g and the supernatant was discarded.

The pellet was then resuspended and lysed at 80° C. for 10 minutes in 80 µl of the following lysis solution (lysis buffer): 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O_8$*2 $H_2O$) and 50 mM TCEP. The pH of this buffer had a pH of 8-9 (samples 1-3). Other samples were contacted with a lysis solution with a pH of 3-4 (samples 4-6). The pH was adjusted using tartaric acid.

The heating step was performed in a 1.5 ml safe-lock Eppendorf tube in a thermal shaker that was pre-warmed at 80° C. before the tubes were introduced into the thermal shaker. The incubation was performed at 1400 rpm for 10 minutes. Importantly, these experimental set-ups did not include the use of an enzyme digestion step.

Afterwards, each of the lysis samples were contacted with 15 µl of clearing solution (2 M $SrCl_2$ in 20 mM Tris and with 20.165 ml/L 15% HCl). Then, the samples were centrifuged, and the supernatant was passed over a column. The column includes a filter/resin made of Resin Sephacryl S400. The supernatant is pressed through the column by centrifuging for 1 minutes at 1000×G.

The obtained nucleic acids were analyzed by photometric measurements as well as by gel electrophoresis. The results of these measurements are depicted in below Table 2.

TABLE 2

Results obtained for spectrophotometric nucleic acid quantification of the different samples.

| Sample | Type of sample | protocol | Nucleic acids (ng/µL) | A260/ A280 | A260/ A230 | A260 | A280 |
|---|---|---|---|---|---|---|---|
| 1 | 200 µL whole blood | alkaline TCEP lysis; pH 8-9; 50 mM TCEP | 32.329 | 1.636 | 1.376 | 0.692 | 0.423 |
| 2 | 200 µL whole blood | alkaline TCEP lysis; pH 8-9; 50 mM TCEP | 30.213 | 1.715 | 1.677 | 0.643 | 0.375 |
| 3 | 200 µL whole blood | akaline TCEP lysis; pH 8-9; 50 mM TCEP | 24.437 | 1.769 | 1.893 | 0.521 | 0.295 |
| 4 | 200 µL whole blood | acidic TCEP-lysis, pH 3-4, 50 mM TCEP | 47.194 | 1.785 | 1.926 | 0.967 | 0.524 |
| 5 | 200 µL whole blood | acidic TCEP-lysis, pH 3-4, 50 mM TCEP | 45.148 | 1.806 | 2.047 | 0.931 | 0.515 |
| 6 | 200 µL whole blood | acidic TCEP-lysis, pH 3-4, 50 mM TCEP | 41.493 | 1.769 | 2.149 | 0.846 | 0.478 |

As can be obtained from Table 2, the spectrophotometric nucleic acid quantification of A260 readings (7$^{th}$ column in Table 1) all lie between 0.1 and 1.0. Thus, these measurements are reliable. This measurement was used for the determination of the final concentration of the obtained nucleic acids as depicted in the 4$^{th}$ column of Table 2.

Furthermore, as shown by the ratio of A260/A280, all samples provide for a ratio close to 1.8. Since pure DNA preparations have an A260/A280 ratio of greater than or equal to 1.8 it is assumed that none of the samples 1-6 includes relevant amounts of additional RNA.

To determine the purity of nucleic acids obtained by the different lysis, the A260/A230 ratio was determined (6$^{th}$ column in Table 2). As shown in above Table 2, the A260/A230 ratio was greater than 1.5 for all samples except for sample 1. This indicates that the nucleic acids of sample 2-6 were of good purity and that non-nucleic acid components were present only in low amounts—if at all.

More specifically, Table 2 shows in general that sufficiently purified nucleic acids can be obtained by both, alkaline and acidic lysis with TCEP. Acidic lysis with TCEP resulted in slightly higher purities of the nucleic acids as evident from the A260/A230 ratios.

Further, the obtained nucleic acids were analyzed by gel electrophoresis. The gel obtained by gel electrophoresis performed with the different samples used in this experiment as depicted in FIG. 2 (nucleic acids obtained by sample 1, 2, 3, 4, 5, and 6 in the respective lanes).

Figure 2:
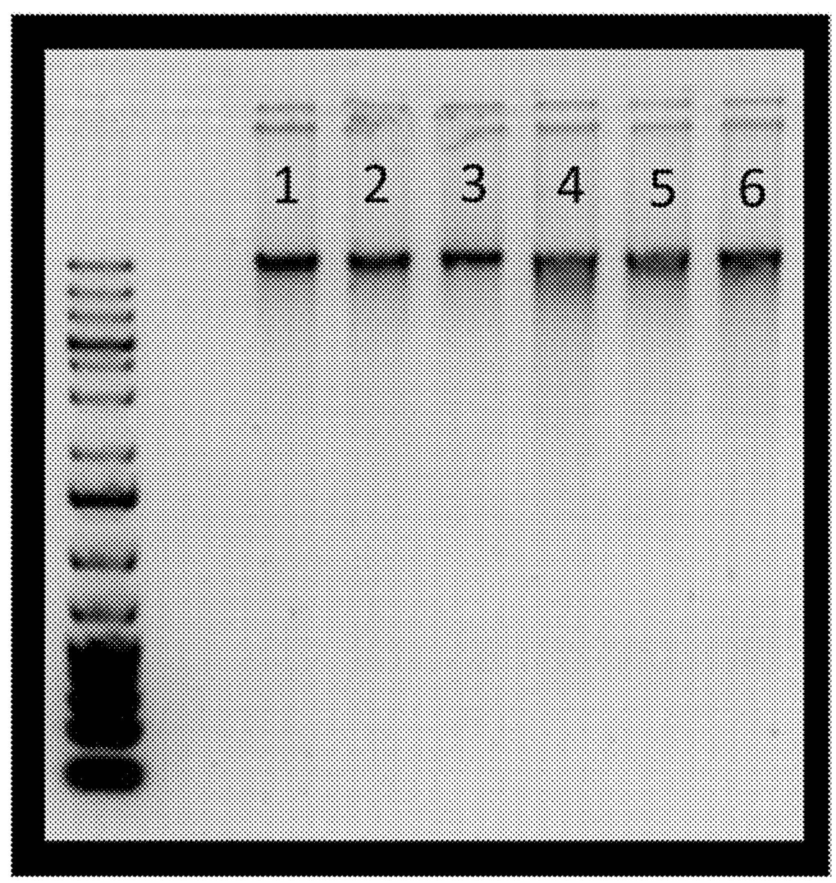

As evident from FIG. 2, all samples provide for a high-molecular-weight band indicating that intact (non-degraded) nucleic acids are present in the tested samples. The low-molecular-weight smears seem to be higher in the acidic conditions than in the alkaline conditions. Thus, the amount of degraded nucleic acids may be higher under acidic conditions than in alkaline conditions.

Example 3: Lysis Using TCEP Concentrations at Neutral pH Compared to a Standard Protocol 200 µl whole blood are used as sample. The sample was washed once with an erythrocyte lysis buffer (10 mM sodium hydrate carbonate ($NaHCO_3$), 155 mM ammonium chloride, 0.1 mM $Na_2EDTA$, pH 7.3). For this washing 1.3 ml of the erythrocyte lysis buffer were added to the sample. The incubation was performed for 3 minutes at room temperature. Afterwards, the sample was centrifuged for 2 minutes at 2000× g and the supernatant was discarded. The pellet was used in the further preparation.

In this first experimental set-up, the lysis included the following steps:

1. Harvesting cells by centrifugation at 2000×g in a 1.5 ml reaction tube and remove supernatant.
2. Adding 55 µl of the lysis solution LS as described above and 25 µl of protease and resuspend cell pellet completely by pulse-vortexing.
3. Place reaction tube in the thermal shaker and incubate at 60° C. for 10 minutes with max. agitation.
4. Add 10 µl of clearing solution (2 M $SrCl_2$ in 20 mM Tris and with 20.165 ml/L 15% HCl) to each lysed sample and vortex vigorously with four pulses of 10 seconds each. The samples become cloudy.
5. Centrifuge for 2 minutes at maximal speed.
6. Transfer lysis supernatant (max. 100 µl) containing the DNA onto a spin column. The column includes a filter/resin made of Resin Sephacryl S400. The supernatant is pressed through the column by centrifuging for 1 minutes at 1000× G.
8. Centrifuge for 1 min at 1000× G. The purified genomic DNA elutes into the 1.5 ml elution tube and can be immediately applied in downstream applications.

On the other hand, in a second experimental setup, 200 µl whole blood as sample was washed once with an erythrocyte lysis buffer (10 mM sodium hydrate carbonate ($NaHCO_3$), 155 mM ammonium chloride, 0.1 mM $Na_2EDTA$, pH 7.3). For this washing 1.3 ml of the erythrocyte lysis buffer were added to the sample. The incubation was performed for 3 minutes at room temperature. Afterwards, the sample was centrifuged for 2 minutes at 2000×g and the supernatant was discarded.

The pellet was then resuspended and lysed at 80° C. for 10 minutes in 80 µl of the following solution (lysis solution): 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O_8$*2 $H_2O$) and 50 mM TCEP. The pH of this buffer had a pH of 7.5. The pH was adjusted using tartraric acid.

The lysis was performed for 3 minutes at 80° C. in a 1.5 ml safe-lock Eppendorf tube in a thermal shaker that was pre-warmed at 80° C. before the tubes were introduced into the thermal shaker. The incubation was performed at 1400 rpm.

Afterwards the lysed cells were contacted with 15 µl of clearing solution (2 M $SrCl_2$ in 20 mM Tris and with 20.165 ml/L 15% HCl). Then the samples were centrifuged, and the supernatant was passed over a column. The column includes a filter/resin made of resin Sephacryl S400. The supernatant is pressed through the column by centrifuging for 1 minutes at 1000× g. Importantly, this experimental setup did not include the use of an enzyme digestion step.

The obtained nucleic acids were analyzed by photometric measurements as well as by gel electrophoresis. The results of these measurements are depicted in below Table 3.

TABLE 3

Results obtained for spectrophotometric nucleic acid quantification of the different samples.

| Sample | Type of sample | protocol | Nucleic acids (ng/µL) | A260/A280 | A260/A230 | A260 | A280 |
|---|---|---|---|---|---|---|---|
| 1 | 200 µL whole blood | enzymatic lysis; 10 min | 19.731 | 1.663 | 1.22 | 0.395 | 0.237 |
| 2 | 200 µL whole blood | enzymatic lysis; 10 min | 28.786 | 1.449 | 0.66 | 0.576 | 0.397 |
| 3 | 200 µL whole blood | enzymatic lysis; 10 min | 22.769 | 1.568 | 1.09 | 0.455 | 0.29 |
| 4 | 200 µL whole blood | neutral TCEP-lysis, pH 7.5; 50 mM TCEP, 3 min | 48.707 | 1.68 | 1.164 | 0.974 | 0.58 |
| 5 | 200 µL whole blood | neutral TCEP-lysis, pH 7.5; 50 mM TCEP, 3 min | 42.291 | 1.731 | 1.095 | 0.846 | 0.489 |
| 6 | 200 µL whole blood | neutral TCEP-lysis, pH 7.5; 50 mM TCEP, 3 min | 43.877 | 1.669 | 0.9 | 0.878 | 0.526 |

As can be obtained from Table 3, the spectrophotometric nucleic acid quantification of A260 readings ($7^{th}$ column in Table 1) all lie between 0.1 and 1.0. Thus, these measurements are reliable. This measurement was used for the determination of the final concentration of the obtained nucleic acids as depicted in the $4^{th}$ column of Table 3. Importantly, the amount of nucleic acids obtained by the "TCEP lysis" is much higher than the amount of nucleic acids obtainable by the standard lysis including a step of enzyme digestion.

Furthermore, the ratio of A260/A280 is higher when the samples were lysed with TCEP (1.68; 1.731 or 1.669 which equals a mean of 1.693) than for samples subjected to enzymatic digestion (1.663, 1.449, 1.568 which equals a mean of 1.56). Therefore, the nucleic acids obtained using the TCEP lysis are of higher quality than the samples treated with a lysis including enzymatic digestion.

To further determine the purity of nucleic acids obtained by the different lysis additionally the A260/A230 ratio was determined ($6^{th}$ column in Table 3). As shown in above Table 3 the A260/A230 ratio was higher for samples treated with the TCEP lysis (1.164, 1.095 and 0.9 which equals a mean of 1.053) than samples subjected to enzymatic digestion (1.22, 0.66, 1.09 which equals a mean of 0.99). Therefore, the nucleic acids obtained using the TCEP solution are of higher purity than the samples treated with a lysis including enzymatic digestion.

Table 3 thus shows that the lysis using a TCEP comprising lysis solution without the use of an enzymatic digestion outperforms standard lysis procedures including a step of enzyme digestion. Further, the lysis is achievable in only 3 minutes compared to 30 minutes of time required by standard protocols requiring enzymatic digestion.

Further, the obtained nucleic acids were analyzed by gel electrophoresis. The gel obtained by gel electrophoresis performed with the different samples used in this experiment is depicted in FIG. 3A (nucleic acids obtained by sample 1, 2, 3, 4, 5, and 6 in the respective lanes).

Figure 3A:
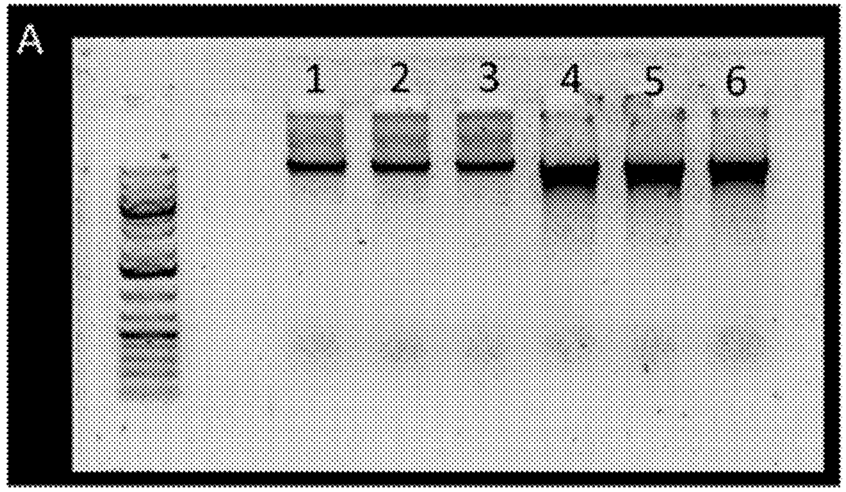

As evident from FIG. 3A, all samples provide for a high-molecular-weight band indicating that intact (non-degraded) nucleic acids are present in the tested samples. Further, the amount of nucleic acids obtained by the TCEP lysis are clearly higher than the amount of nucleic acids obtained by a lysis including enzymatic digestion.

The eluates obtained after lysis were additionally directly—without any further modification—analyzed by real time PCR (RT-PCR). In a real time PCR assay a positive reaction is detected by accumulation of a fluorescent signal. The Ct (cycle threshold) is defined as the number of cycles required for the fluorescent signal to cross the threshold (i.e. exceeds background level). Ct levels are inversely proportional to the amount of target nucleic acid in the sample (i.e. the lower the Ct level the greater the amount of target nucleic acid in the sample). Typically, Cts<29 are strong positive reactions indicative of abundant target nucleic acid in the sample, Cts of 30-37 are positive reactions indicative of moderate amounts of target nucleic acid and Cts of 38-40 are weak reactions indicative of minimal amounts of target nucleic acid.

In this experiment, the Ct values as depicted in below Table 4 have been obtained.

TABLE 4

Results obtained for RT-PCR of the different samples.

| sample | Ct | protokol |
|---|---|---|
| 1 | 23.12 | enzymatic lysis |
| 2 | 22.41 | enzymatic lysis |
| 3 | 23.12 | enzymatic lysis |
| 4 | 21.38 | neutral TCEP lysis |
| 5 | 21.06 | neutral TCEP lysis |
| 6 | 20.72 | neutral TCEP lysis |

Figure 3B:
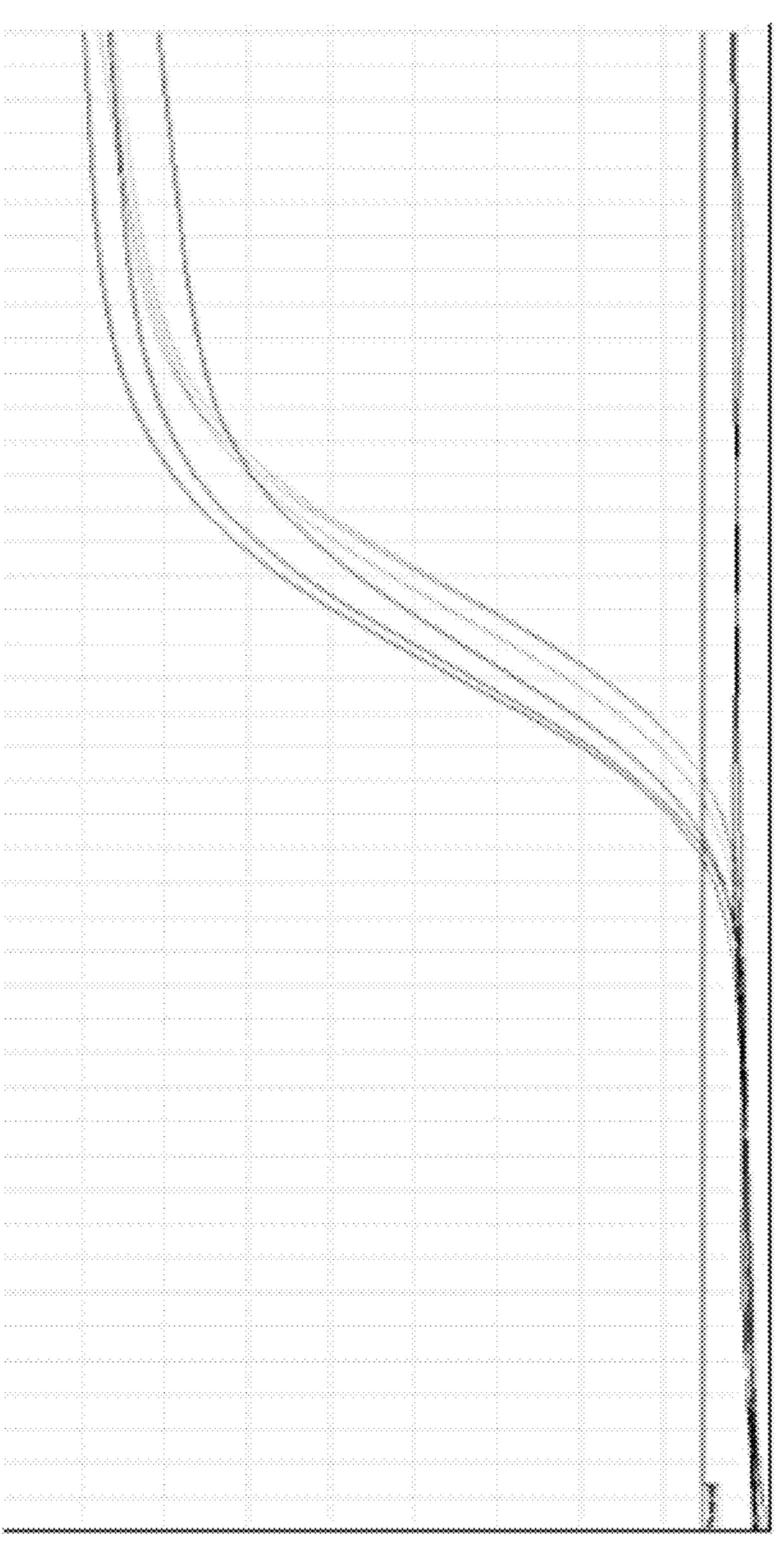

The according PCR graph is depicted in FIG. 3B. The RT-PCR data confirm that the amount of nucleic acids obtained by the "TCEP lysis" is higher and of better quality/purity than the amount of nucleic acids obtainable by the standard lysis including a step of enzyme digestion.

Example 4: TCEP Lysis Also Efficient in Muscle Tissue

To test the lysis as described herein in further samples the following experiment was performed. Some samples of 30 mg rat muscle tissue were mixed with 100 µl of beadbeating buffer (20 mM Tris, 0.1 mM $Na_2EDTA$, 100 mM TCEP, pH 7.5). Directly afterwards 100 µl of solution (lysis buffer) of the following components: 25 mM TRIS ($C_4H_{11}NO_3$), 70 mM SDS, 50 mM ammonium chloride and 0.1 mM $Na_2EDTA$ with a pH of 8 (the pH is adjusted with HCl) were added.

Other samples containing 30 mg rat muscle tissue were mixed with 100 µl of beadbeating buffer (20 mM Tris, 0.1 mM $Na_2EDTA$, 100 mM TCEP, pH 7.5). Then beadbeating was performed. Afterwards 100 µl of solution (lysis solution) of the following components: 25 mM TRIS ($C_4H_{11}NO_3$), 70 mM SDS, 50 mM ammonium chloride and 0.1 mM $Na_2EDTA$ with a pH of 8 (the pH is adjusted with HCl) were added.

The incubation was performed for 3 minutes at 80° C. in a 1.5 ml safe-lock Eppendorf tube in a thermal shaker that was pre-warmed at 80° C. before the tubes were introduced into the thermal shaker. The incubation was performed at 1400 rpm.

Afterwards the lysed cells were contacted with 25 µl of clearing solution (2 M $SrCl_2$ in 20 mM Tris and with 20.165 ml/L 15% HCl). Then, the samples were centrifuged, and the supernatant was passed over a column. The column includes a filter/resin made of resin Sephacryl S400. The supernatant is pressed through the column by centrifuging for 1 minute at 1000× g. Importantly, this experimental setup did not include the use of an enzyme digestion step.

The obtained nucleic acids were analyzed by photometric measurements. The results of these measurements are depicted in below Table 5 A and 5B (FIG. 8). Table 5A:

TABLE 5

Results obtained for lysis with lysis buffer including TCEP without beadbeating (Table 5A) and with beadbeating (Table 5B, presented in FIG. 8).

| sample | Type of sample | protocol | Nucleic acid (ng/µL) | A260/ A280 | A260/ A230 | A260 | A280 |
|---|---|---|---|---|---|---|---|
| 1 | 30 mg rat muscle | TCEP-lysis | 13.967 | 1.574 | 0.623 | 0.279 | 0.177 |
| 2 | 30 mg rat muscle | TCEP-lysis | 20.56 | 2.046 | 0.323 | 0.411 | 0.201 |
| 3 | 30 mg rat muscle | TCEP-lysis | 20.606 | 1.657 | 0.442 | 0.412 | 0.249 |

As can be obtained from Table 5, the spectrophotometric nucleic acid quantification of A260 readings ($7^{th}$ column in Table 1) essentially all lie between 0.1 and 1.0. Thus, these measurements are reliable. This measurement was used for the determination of the final concentration of the obtained nucleic acids as depicted in the $4^{th}$ column of Table 5. Table 5 thus shows that the lysis using a TCEP comprising lysis solution without the use of an enzymatic digestion can also be used for lysing muscle tissue.

Example 5: TCEP Lysis Also Efficient in Sperm Samples

To test the lysis as described herein in further samples the following experiment was performed. 30 µl swine sperm was lysed using different lysis solutions (lysis buffers).

30 µl of sperm were contacted with 1.3 erythrocyte lysis buffer as disclosed in Example 2 and incubated for 3 minutes at room temperature. Then, the sample was centrifuged for 2 minutes at 2000 g and the supernatant was discarded.

The pelleted sperm was resuspended and lysed using 80 µl solution (lysis solution) of the following components: 50 mM TCEP, 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O_8$*2

$H_2O$), 50 mM ammonium chloride with a pH of 10, 9, 8 or 7. The pH was adjusted with NaOH where necessary. The lysis was performed for 10 minutes at 80° C. in a 1.5 ml 1.5 ml safe-lock Eppendorf tube in a thermal shaker that was pre-warmed at 80° C. before the tubes were introduced into the thermal shaker. The incubation was performed at 1400 rpm.

Afterwards the lysed cells were contacted with 15 µl of clearing solution (2 M $SrCl_2$ in 20 mM Tris and with 20.165 ml/L 15% HCl). Then, the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in below Table 6.

TABLE 6

Results obtained for lysis with lysis buffer including TCEP without enzyme digestion.

| Sample | Type of sample | protocol | Nucleic acids (ng/µL) | A260/ A280 | A260/ A230 | A260 | A280 |
|---|---|---|---|---|---|---|---|
| 1 | 30 µL sperm | TCEP-lysis; pH 10.3 | 98.93 | 1.799 | 1.858 | 2.03 | 1.128 |
| 2 | 30 µL sperm | TCEP-lysis; pH 10.3 | 98.323 | 1.82 | 1.07 | 1.995 | 1.096 |
| 3 | 30 µL sperm | TCEP-lysis; pH 9.1 | 116.46 | 1.826 | 1.576 | 2.434 | 1.333 |
| 4 | 30 µL sperm | TCEP-lysis; pH 9.1 | 128.289 | 1.824 | 1.543 | 2.592 | 1.421 |
| 5 | 30 µL sperm | TCEP-lysis; pH 8.2 | 126.874 | 1.811 | 1.371 | 2.591 | 1.43 |
| 6 | 30 µL sperm | TCEP-lysis; pH 8.2 | 123.353 | 1.824 | 1.291 | 2.517 | 1.38 |
| 7 | 30 µL sperm | TCEP-lysis; pH 7.2 | 105.408 | 1.822 | 1.323 | 2.149 | 1.18 |
| 8 | 30 µL sperm | TCEP-lysis; pH 7.2 | 124.242 | 1.827 | 1.609 | 2.546 | 1.394 |

Table 6 shows that the spectrophotometric nucleic acid quantification of A260 readings ($7^{th}$ column in Table 1) all lie between 0.1 and 1.0. Thus, these measurements are reliable. This measurement was used for the determination of the final concentration of the obtained nucleic acids as depicted in the $4^{th}$ column of Table 6.

Table 6 thus shows that the lysis using a TCEP comprising lysis solution without the use of an enzymatic digestion can also be used for lysing sperm, wherein the lysis buffer can be used at different pH.

Example 6: TCEP Lysis Also Efficient in Plant Samples

To test the lysis as described herein in further samples, the following experiment was performed. About 10 mg fresh cotyledon of potato were contacted with 100 µl beating buffer (20 mM TRIS, 0.1 mM $Na_2EDTA$, 100 mM TCEP at a pH of 7.5) Then the samples were beadbeated for 5 minutes. Afterwards the samples were centrifuged for 1 minute at 1000 g. Then the samples were lysed using 80 µl a lysis solution (lysis buffer) of the following components: 25 mM TRIS ($C_4H_{11}NO_3$), 70 mM SDS, 50 mM ammonium chloride and 0.1 mM $Na_2EDTA$ with a pH of 8 (the pH is adjusted with HCl) in a 96 well plate.

The lysis was performed for 10 or 15 minutes at 80° C. in a 1.5 ml safe-lock Eppendorf tube in a thermal shaker that was pre-warmed at 80° C. before the tubes were introduced into the thermal shaker. The incubation was performed at 1400 rpm.

Afterwards the lysed cells were contacted with 50 µl of clearing solution (2 M $SrCl_2$ in 20 mM Tris and with 20.165 ml/L 15% HCl). Then the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in below Table 7.

TABLE 7

Results obtained for lysis with lysis buffer including TCEP without enzyme digestion.

| | Content [ng/µL] | Ratio A260/230 | Ratio A260/280 |
|---|---|---|---|
| 50 mM TCEP, 10 min, 80° C. | 22.55 | 0.90 | 1.61 |
| 50 mM TCEP, 15 min, 80° C. | 36.14 | 1.00 | 1.77 |

Table 7 confirms that nucleic acids can also be obtained from plant samples when using the TCEP lysis. Longer lysis at 80° C. increased the amount of nucleic acids obtained.

Example 7: Using Reduction Agents Other than TCEP

To understand if the positive effect of TCEP in the lysis buffer can also be observed with other reducing agents, the following experiment has been performed.

Bacterial (*P. fluorescence*) samples were centrifuged. The samples were then resuspended in 100 µ of solution (lysis solution) of the following components: 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O*2\ H_2O$) and 50 mM ammonium chloride. The pH of this buffer was set at 8 by the addition of HCl. The samples were incubated for 5 minutes at 80° C. in a 1.5 ml safe-lock Eppendorf tube in a thermal shaker that was pre-warmed at 80° C. before the tubes were introduced into the thermal shaker. The incubation was performed at 1400 rpm.

Afterwards the lysed cells were contacted with 10 µl of clearing solution (1 M $SrCl_2$ in 20 mM Tris/HCl of pH 8). Then the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in Table 8 (presented in FIG. 9).

As can be obtained from Table 8, the ratio of A260/A280 and the A260/A230 ratio are comparable for all reducing agents used in lysis. Thus, the purity and quality of the nucleic acids obtained by the different lysis solutions (including different reducing agents) seems to be similar as well. The lysis using TCEP yielded the highest total amount of nucleic acids. This value was set at 100%. The total yield of nucleic acids obtained by the further tested lysis solutions was calculated in comparison to this 100% yield. The threshold for a sufficient yield was set at at least 25%. This has also been done in view of the results obtained without any reducing agent additive as explained in Example 9. In accordance with Table 8, the reducing agents TCEP, N-acetylcysteamine, sodium hydrosulfite (Na-hydrosulfite) and glutathione (L-Glutathione red.) provided for sufficient amounts of nucleic acids (more or equal than 25% yield of the yield obtained when using TCEP). On the other hand, the reducing agents sodium thiosulfate-5-hydrate (Na-thiosulfate-5-hydrate), and 1-propanethiol did not provide for sufficient amounts of nucleic acids (below 25%).

As can be seen from the A260/A230 lysis with all the different reducing agents resulted high purity/quality of nucleic acids (all have a ratio close to 1.8).

Example 8: Using Reduction Agents Other than TCEP

To understand if the positive effect of TCEP in the lysis solution (buffer) can also be overserved with other reducing agents, the following experiment has been performed.

Bacterial (*P. fluorescence*) samples were centrifuged. The samples were then resuspended in 100 µl of lysis solution (lysis buffer) of the following components: 20 mM of indicated reducing agent, 50 mM Tris ($C_4H_{11}NO_3$), 70 mM SDS ($C_{12}H_{25}NaO_4S$), $Na_2EDTA$ ($C_{10}H_{14}N_2Na_2O_8$*2 $H_2O$), 50 mM ammonium chloride. The pH of this buffer was set at 8 by the addition of HCl. The samples were incubated for 5 minutes at 80° C. as described herein.

Afterwards the lysed cells were contacted with 10 µl of clearing solution (1 M $SrCl_2$ in 20 mM Tris HCl of pH 8). Then the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in Table 9 (presented in FIG. 10).

As can be obtained from Table 9, the ratio of A260/A280 and the A260/A230 ratio are comparable for all reducing agents used in lysis. Thus, the purity and quality of the nucleic acids obtained by the different lysis solutions (including different reducing agents) seems to be similar as well. As can be seen from the A260/A230 lysis with all the different reducing agents resulted high purity/quality of nucleic acids (all have a ratio close to 1.8).

The lysis using TCEP yielded the highest total amount of nucleic acids. This value was set at 100%. The total yield of nucleic acids obtained by the further tested lysis solutions was calculated in comparison to this 100% yield. The threshold for a sufficient yield was set at at least 25%. This has also been done in view of the results obtained without any reducing agent as explained in Example 9.

In accordance with Table 9, the reducing agents TCEP and L-cysteine hydrochloride provided for sufficient amounts of nucleic acids (more or equal than 25% yield of the yield obtained when using TCEP). On the other hand, the reducing agents ammonium thioglycolate, sodium thioglycolate (Na thioglycolate) and DTT did not provide for sufficient amounts of nucleic acids (below 25%).

Example 9: Using Reduction Agents Other than TCEP with Prolonged Lysis

To understand if the positive effect of TCEP in the lysis buffer can also be overserved with other reducing agents under longer lysis the following experiment has been performed.

Bacterial (*P. fluorescence*) samples were centrifuged. The samples were then resuspended in 100 µl of lysis solution (lysis buffer) of the following components: 20 mM of indicated reducing agent, 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O$*2 $H_2O$) and 50 mM ammonium chloride. The pH of this buffer was set at 8 by the addition of HCl. The samples were incubated for 10 minutes at 80° C. as described above.

Afterwards the lysed cells were contacted with 10 µl of clearing solution (1 M $SrCl_2$ in 20 mM Tris/HCl of pH 8). Then the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in Table 10 (presented in FIG. 11).

As can be obtained from Table 9, the ratio of A260/A280 and the A260/A230 ratio are comparable for all reducing agents used in lysis. Thus, the purity and quality of the nucleic acids obtained by the different lysis solutions (including different reducing agents) seems to be similar as well. As can be seen from the A260/A230 lysis with all the different reducing agents resulted high purity/quality of nucleic acids (all have a ratio close to 1.8).

The lysis using TCEP yielded the highest total amount of nucleic acids. This value was set at 100%. The total yield of nucleic acids obtained by the further tested lysis solutions was calculated in comparison to this 100% yield. The threshold for a sufficient yield was set at at least 25%. This has also been done in view of the results obtained without any reducing agent as explained in Example 9.

In accordance with Table 10, the reducing agents TCEP, sodium hydrosulfite (Na-hydrosulfite), glutathione (L-glutathione red.), ammonium thioglycolate, L-cysteine hydrochlorid and sodium sulfite (Na-sulfite) provided for sufficient amounts of nucleic acids (more or equal than 25% yield of the yield obtained when using TCEP). On the other hand, the reducing agents N-acetlycysteamine and sodium thiosulfate (Na-thiosulfate) did not provide for sufficient amounts of nucleic acids (below 25%) using the longer lysis times.

Example 10: Effect of SDS on Lysis Efficiency in Combination with TCEP

To understand SDS is required in the lysis solution comprising a reducing agent as described herein, the following experiment has been performed.

Three different lysis solutions were prepared. Lysis solution TCEP TE-BE consisting of the following compounds: 20 mM of TCEP and 0.1 mM EDTA with a pH of 7; lysis solution TCEP in cell buffer consisting of the compounds 20 mM of TCEP, 70 mM SDS ($C_{12}H_{25}NaO_4S$), 0.1 mM $Na_2EDTA$ ($C_{10}H_{14}N_2Na_2O_8$*2 $H_2O$) and 50 mM ammonium chloride; lysis solution cell buffer consisted of the compounds: 25 mM TRIS, 70 mM SDS ($C_{12}H_{25}NaO_4S$), 0.1 mM $Na_2EDTA$ ($C_{10}H_{14}N_2Na_2O$*2 $H_2O$) and 50 mM ammonium chloride. The pH of this buffer was set at 7-8 by the addition of HCl.

Afterwards, the lysed cells were contacted with 10 μl of clearing solution (1 M $SrCl_2$ in 20 mM Tris/HCl of pH 8). Then the samples were centrifuged, and the supernatant was passed over a column. The column includes a filter/resin made of Resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in Table 11 (presented in FIG. 12).

Table 11 shows that the highest amounts of nucleic acids are obtained when the reducing agent (here TCEP) is used in combination with a detergent (e.g. SDS). Omission of either the detergent (63.33% of the amount obtained when using the reducing agent in combination with detergent, which equals 100%) or of the reducing agent (30.28% of the amount obtained when using the reducing agent in combination with detergent, which equals 100%) reduces the amount of nucleic acids obtained.

As can be seen from the A260/A230 ratio lysis resulted high purity/quality of nucleic acids (all have a ratio close to 1.8).

Example 11: Performing the Lysis with Different Conditions

To understand the impact different parameters and especially the temperature has on the lysis, different experimental set ups were compared. Specifically, the temperature was varied from 80° C., 60° C. to 40° C., while the pH was varied from pH 10, pH 7 to pH 4, the TCEP concentration was varied from 50 mM to 5 mM and the incubation time of the lysis sample at a specific temperature was 10 minutes.

1 ml of a culture of *Pseudomonas flourescens* was centrifuged. The pellet was resuspended in 90 μl of different lysis solutions. Different amounts of TCEP (5 mM and 50 mM) were solved in 25 mM TRIS, 70 mM SDS, 50 mM ammonium chloride, 0.1 mM $Na_2EDTA$. Afterwards the pH was adjusted to 10, 7 or 4 with HCl or NaOH.

Afterwards, the lysed cells were contacted with 10 μl of clearing solution (2 M $SrCl_2$ in 20 mM Tris in 20.165 ml/L HCl). Then the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained results are summarized in Table 12 (presented in FIG. 13).

Table 12 shows that the highest amounts of nucleic acids are obtained when the lysis is performed at a temperature of 60° C. or 80° C. When the lysis is performed at 40° C. much lower amounts of nucleic acids are obtained. Sufficient amounts of nucleic acids are thus obtainable at a lysis temperature of at least about 60° C. or higher. In summary Table 12 shows:

- higher temperatures (60 and 80° C.) result in unexpectedly high amounts of nucleic acids;
- longer time of lysis can increase the obtained amount of nucleic acids;
- a neutral or acidic pH can increase the obtained amount of nucleic acids, especially when the temperature, time of lysis are not optimally selected. The data point in #7 is incorrect, (erroneous measurement) and was therefore deleted.

Example 12: Using Reducing Agents with Structural Similarities to TCEP 1 ml over night cultures of *P. fluorescence* and *A. Bohemicus* were cleaned and centrifuged to form a cell pellet. A lysis solution comprising 50 mM Tris ($C_4H_{11}NO_3$), 70 mM SDS ($C_{12}H_{25}NaO_4S$), $Na_2EDTA$ ($C_{10}H_{14}N_2Na_2O_8$*2 $H_2O$), 50 mM ammonium chloride and either 20 mM Tris(hydroxy methyl)phosphine, Tris(hydroxy ethyl)phosphine or Tris(hydroxypropyl)phosphine at pH 8 were prepared. Then 80 μl of lysis solution were added to cell pellets of the above described cell cultures. Lysis was performed for 3 minutes at 80° C. as described elsewhere herein.

Afterwards the lysed cells were contacted with 15 μl of clearing solution (2 M $SrCl_2$ in aqua dest. Then the samples were centrifuged, and the supernatant was passed over a column. The column includes a filter/resin made of Resin Sephacryl S400. The supernatant is pressed through the column by centrifuging for 1 minute at 1000× G. Importantly, this experimental setup did not include the use of an enzyme digestion step.

The obtained nucleic acids were analyzed by photometric measurements. The results of these measurements are depicted in the below Table.

The obtained results are summarized in below Table 13.

TABLE 13

Results obtained for lysis with lysis buffer including different reducing agents.

| # | Sample | reducing agent | total μg of nucleic acids | mean 260/280 | mean 260/230 | mean μg of total nucleic acids | indication |
|---|---|---|---|---|---|---|---|
| 1 | P. fluorescence | Tris(hydroxy methyl)phosphine | 45.61 | 2.09 | 1.77 | 38.84 | 3 minutes |
| 2 | P. fluorescence | Tris(hydroxy methyl)phosphine | 37.61 | | | | of lysis |

TABLE 13-continued

Results obtained for lysis with lysis buffer including different reducing agents.

| # | Sample | reducing agent | total µg of nucleic acids | mean 260/280 | mean 260/230 | mean µg of total nucleic acids | indication |
|---|---|---|---|---|---|---|---|
| 3 | P. fluorescence | Tris(hydroxy methyl)phosphine | 33.29 | | | | |
| 4 | P. fluorescence | Tris(hydroxy ethyl)phosphine | 62.18 | 2.02 | 2.1 | 64.25 | 3 minutes |
| 5 | P. fluorescence | Tris(hydroxy ethyl)phosphine | 64.65 | | | | of lysis |
| 6 | P. fluorescence | Tris(hydroxy ethyl)phosphine | 65.91 | | | | |
| 7 | P. fluorescence | Tris(hydroxypropyl)phosphine | 37.37 | 2.02 | 1.99 | 35.54 | 3 minutes |
| 8 | P. fluorescence | Tris(hydroxypropyl)phosphine | 30.97 | | | | of lysis |
| 9 | P. fluorescence | Tris(hydroxypropyl)phosphine | 38.29 | | | | |
| 10 | A. Bohemicus | Tris(hydroxy methyl)phosphine | 40.19 | 2.07 | 1.83 | 45.15 | 3 minutes |
| 11 | A. Bohemicus | Tris(hydroxy methyl)phosphine | 38.95 | | | | of lysis |
| 12 | A. Bohemicus | Tris(hydroxy methyl)phosphine | 56.32 | | | | |
| 13 | A. Bohemicus | Tris(hydroxy ethyl)phosphine | 79.79 | 2 | 1.5 | 72.51 | 3 minutes |
| 14 | A. Bohemicus | Tris(hydroxy ethyl)phosphine | 65.32 | | | | of lysis |
| 15 | A. Bohemicus | Tris(hydroxy ethyl)phosphine | 72.42 | | | | |
| 16 | A. Bohemicus | Tris(hydroxypropyl)phosphine | 36.08 | 2.01 | 1.43 | 38.98 | 3 minutes |
| 17 | A. Bohemicus | Tris(hydroxypropyl)phosphine | 37.18 | | | | of lysis |
| 18 | A. Bohemicus | Tris(hydroxypropyl)phosphine | 43.67 | | | | |

Table 13 shows that all reducing agents tried in this experiment provide for nucleic acids of good quality.

Example 13: Lysis with Tris(Hydroxy Methyl)Phosphine in Comparison to TCEP and Subsequent PCR Analysis 1 ml over night cultures of *M. luteus* or *B. subtilis* were cleaned and pelleted by centrifugation. The cell pellet was resuspended with 90 µl lysis solution comprising 50 mM Tris ($C_4H_{11}NO_3$), 70 mM SDS ($C_{12}H_{25}NaO_4S$), 0.1 mM $Na_2EDTA$ ($C_{10}H_{14}N_2Na_2O$*2 $H_2O$), 50 mM ammonium chloride and 20 mM Tris(hydroxy methyl)phosphine or TCEP at pH 8. The lysis took place for 3 minutes at 80° C. as described elsewhere herein.

Alternatively, the lysis was performed using a lysis enzyme. Samples were resuspended in 150 µl of 10 mg/ml lysozym in TE-Bioecho. The enzyme lysis took place for 5 min at 37° C. Afterwards, the samples were centrifuged for 3 min 2000× G. The supernatant was removed and the pellet was then contacted with the lysis solution and treated as described above.

Afterwards, the lysed cells were contacted with 15 µl of clearing solution (2 M $SrCl_2$ in aqua dest.). The addition of the clearing solution has the effect that anionic detergents are precipitated. Then the samples were centrifuged, and the supernatant was passed over a column. The column includes a filter/resin made of resin Sephacryl S400. The supernatant is pressed through the column by centrifuging for 1 minute at 1000× G. Importantly, this experimental setup did not include the use of an enzyme digestion step.

The obtained results are summarized in Table 14 (presented in FIG. 14).

Table 14 shows that the agents tried in this experiment provide for nucleic acids of good quality. The additional enzyme digestion step slightly increased the yield of obtained nucleic acid. The obtained nucleic acids—for the *B. subtilis* samples—were subsequently analyzed by PCR. The results are summarized in above Table 14 as well.

Example 14: Comparison of Anionic and Non-Ionic Detergents

To be able to compare the results for anionic vs. non-ionic detergents, the following experimental set ups were established.

For gram negative bacteria:

The Lysis Buffer Composition was as Follows:

70 mM detergent (anionic: SDS, Li-DS; non-ionic: Triton X-100),
50 mM TCEP,
0.1 mM EDTA,
25 mM TRIS, and
50 mM Ammoniochloride,
pH=7.5 (adjusted with NaOH).

The Applied Clearing Solution Included the Following Components:

2 M $SrCl_2$, and
20 mM TRIS,
adjusted with 20.165 ml/L 15% HCl.

the Following Protocol has been Carried Out:

1 ml of a culture of *Escherichia coli* was centrifuged at 5000×g for 3 minutes and the supernatant was discarded. The pellet was then resuspended in 100 µL lysis buffer and incubated at 80° C. for 3 minutes. In the case of SDS or LIDS containing lysis buffers, 15 µL of clearing solution were added after incubation. In the case of Triton X-100 containing lysis buffer, only 15 µL of A. dest was added.

Then, the samples were centrifuged at 20000×g, and the supernatant was passed over a column. The column included a filter/resin made of resin Sephacryl S400. The supernatant was processed through the column by centrifuging for 1 minute at 1000× g. Importantly, this experimental setup did not include the use of an enzyme digestion step, leading to a huge reduction of required time compared to a set up, which requires an enzyme digestion step.

The obtained nucleic acids were analyzed by photometric measurements as well as by gel electrophoresis (see following analysis).

Photometric Measurement:

Table 15 (presented as FIG. 15) shows results obtained for samples with different detergents with regard to nucleic acid concentration, A260/A280 and A260/A230.

Samples 1-8 (anionic detergents SDS and LiDS) showed high nucleic acid concentrations and high purity (A260/280 ratio and A260/230 ratio). Also, the absorbance spectrum of the samples 1-8 showed a clean nucleic acid peak at 260 nm, indicating a highly pure nucleic acid sample.

Samples 9-12 (non-ionic detergent Triton X-100) showed are highly impure sample (very low A260/280 ratios and very low A260/230 ratios). Furthermore, the absorbance spectrum showed no nucleic acid peak at 260 nm at all. Moreover, there were strong impurities between 260 nm-290 nm and at 230 nm. Since all other lysis buffer components were unchanged, this impurity was caused due to Triton X-100 in the sample, which was not properly removed during the isolation. Thus, a contamination with Triton X-100 in the sample can lead to unwanted problems in downstream applications (e.g. enzymatic reactions).

It is therefore clear, by the results obtained by this experiment of Example 14, that a lysis buffer comprising Triton X-100 is not suitable for the isolation of nucleic acids.

Figure 4A:
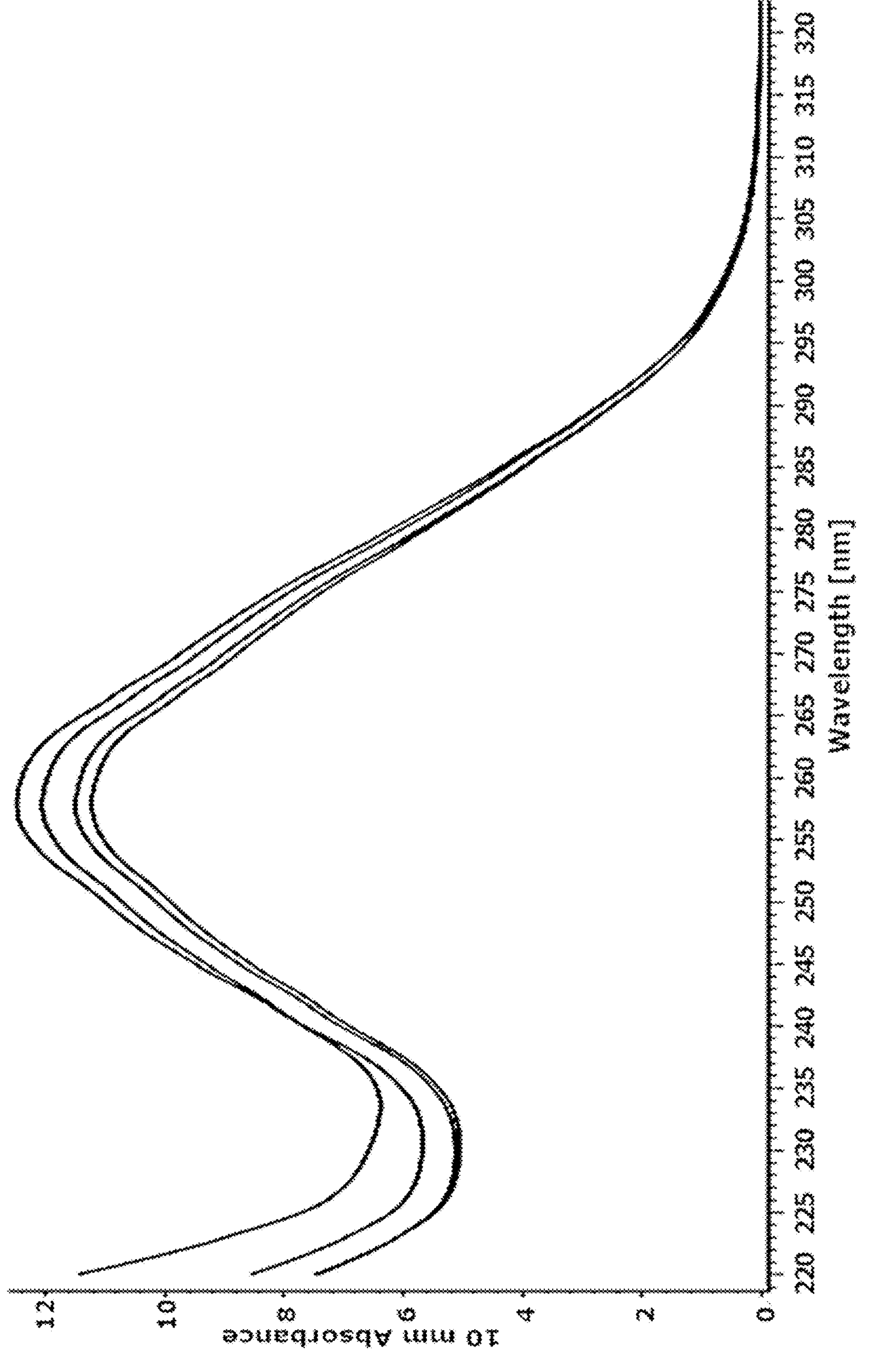
Figure 4B:
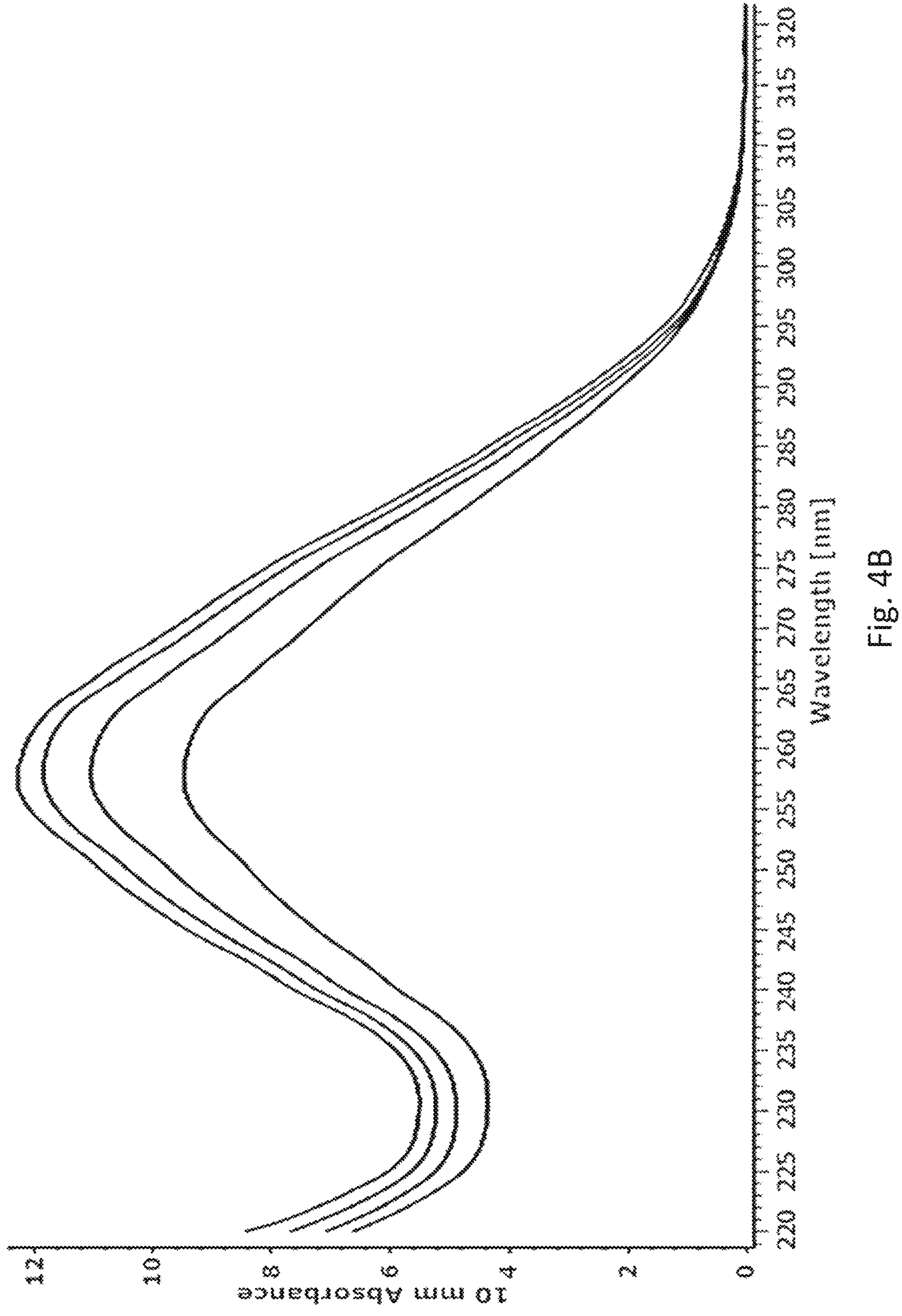
Figure 4C:
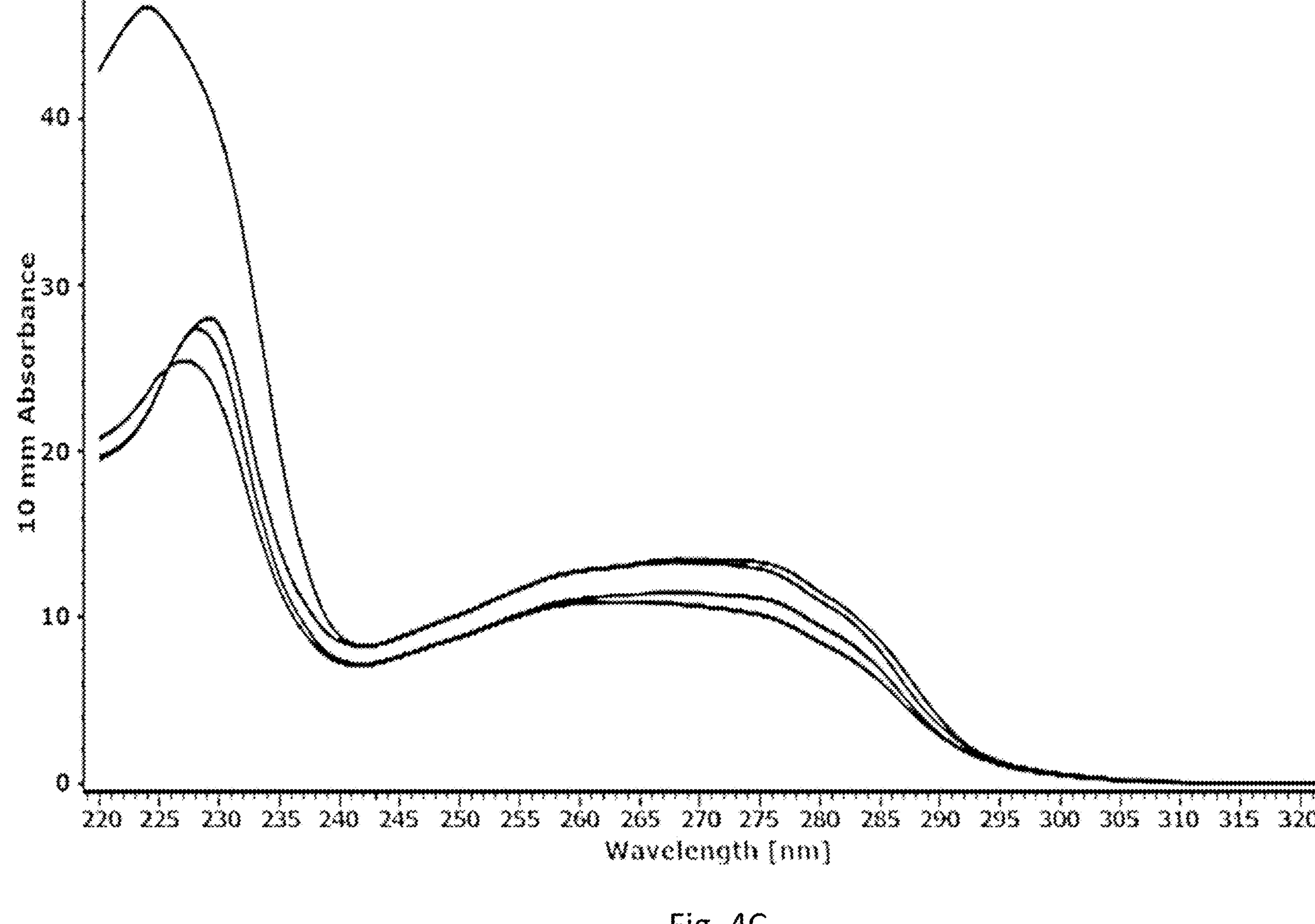

For samples 1-4, the respective photometric measurement is shown in FIG. 4A. For samples 5-8, the respective photometric measurement is shown in FIG. 4B. For samples 9-12, the respective photometric measurement is shown in FIG. 4C.

Figure 5:
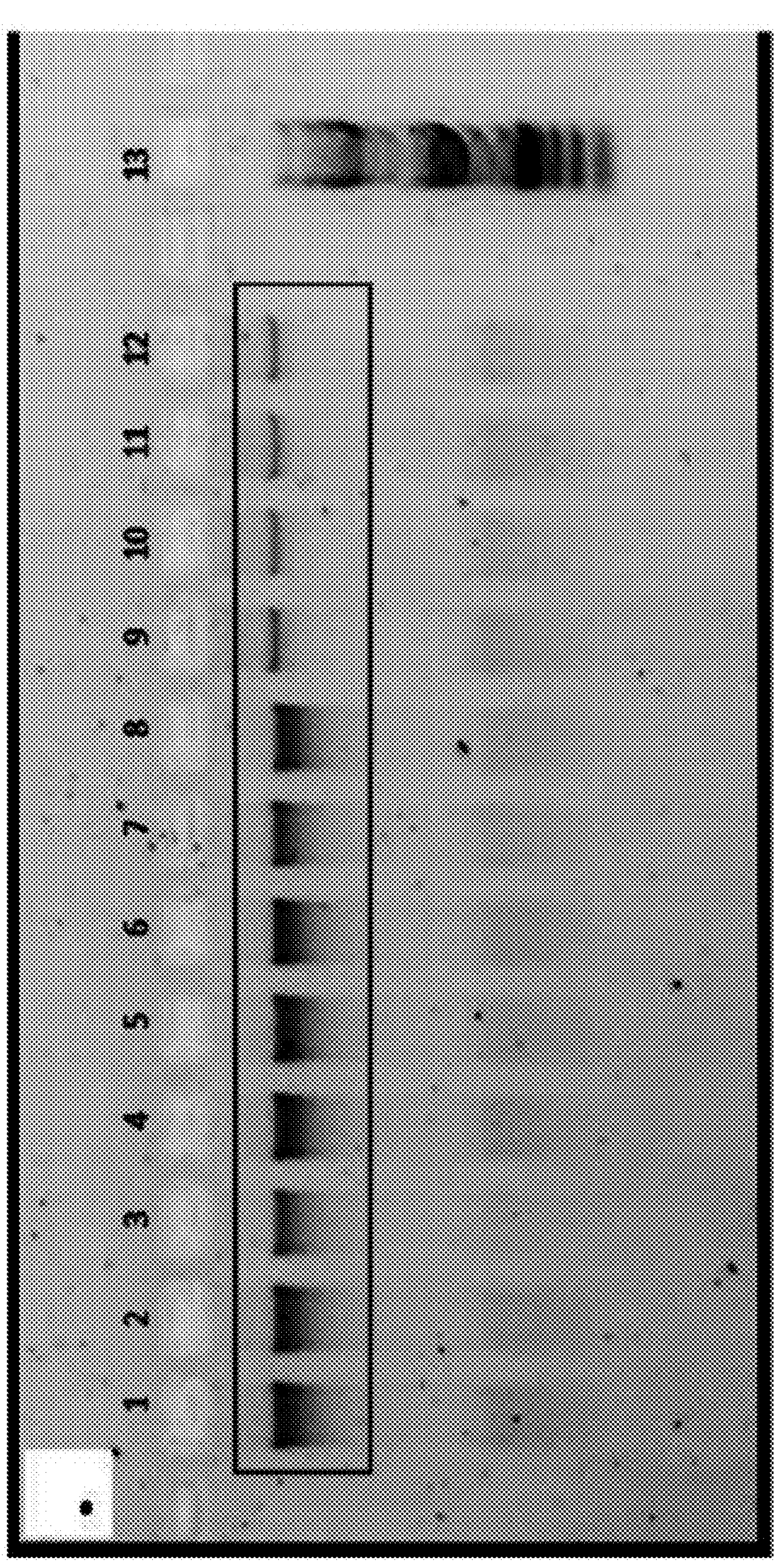

Gel Electrophoresis:

The respective gel electrophoresis shown in FIG. 5 revealed that samples 1-8 showed a strong band of genomic DNA (marked in red), indicating a successful DNA isolation out of the bacteria using anionic detergents (SDS and LiDS). In contrast, samples 9-12 show only a very thin and weak band of genomic DNA (also marked in red), indicating only a weak and partial DNA isolation.

Therefore, the results indicate that a lysis buffer comprising Triton X-100 as a detergent is not suitable for the isolation of nucleic acids out of gram negative bacteria.

For Human Blood:

The Lysis Buffer Composition was as Follows:

- 70 mM detergent (anionic SDS or anionic LiDS or non-ionic: Triton X-100),
- 50 mM TCEP,
- 0.1 mM EDTA,
- 25 mM TRIS, and
- 50 mM Ammoniumchlorid,
- pH=7.5 (adjusted with NaOH).

The applied clearing solution included the following components:

- 2 M $SrCl_2$,
- 20 mM TRIS, and
- adjusted with 20.165 ml/L 15% HCl.

The Following Protocol has been Carried Out:

500 μl whole blood was used as sample. The sample was washed once with an erythrocyte lysis buffer (10 mM sodium hydrate carbonate ($NaHCO_3$), 155 mM ammonium chloride, 0.1 mM $Na_2EDTA$, pH 7.3). For this washing, 1.3 ml of the erythrocyte lysis buffer was added to the sample. The incubation was performed for 3 minutes at room temperature. Afterwards, the sample was centrifuged for 2 minutes at 2000× g and the supernatant was discarded. The pellet was used in the further preparation. The pellet was then resuspended in 100 μL lysis buffer and incubated at 80° C. for 3 minutes. In the case of SDS or LiDS containing lysis buffers, 15 μL of clearing solution were added after incubation. In the case of Triton X-100 containing lysis buffer, only 15 μL of A. dest was added.

Then, the samples were centrifuged at 20000×g, and the supernatant was passed over a column. The column included a filter/resin made of resin Sephacryl S400. The supernatant was processed through the column by centrifuging for 1 minute at 1000× g. Importantly, this experimental set up did not include the use of an enzyme digestion step, leading to a huge reduction of required time compared to a set up, which requires an enzyme digestion step.

The obtained nucleic acids were analyzed by photometric measurements as well as by gel electrophoresis (see following analysis).

Photometric Measurement:

Table 16 (presented as FIG. 16) shows results obtained for samples with different detergents with regard to nucleic acid concentration, A260/A280 and A260/A230.

Samples 1-8 (anionic detergents SDS and LiDS) showed high nucleic acid concentrations and high purity (A260/280 ratio and A260/230 ratio). Also, the absorbance spectrum of the samples 1-8 showed a clean nucleic acid peak at 260 nm, indicating a highly pure nucleic acid sample.

Samples 9-12 (non-ionic detergent Triton X-100) showed highly impure sample (very low A260/280 ratios and very low A260/230 ratios). Furthermore, the absorbance spectrum showed no nucleic acid peak at 260 nm at all. Moreover, there were strong impurities between 260 nm-290 nm and at 230 nm. Since all other lysis buffer components were unchanged, this impurity was caused due to Triton X-100 in the sample, which was not properly removed during the isolation. A contamination with Triton X-100 in the sample can lead to unwanted problems in downstream applications (e.g. enzymatic reactions).

It is therefore clear, by the results obtained by this experiment of Example 14, that a lysis buffer comprising Triton X-100 is not suitable for the isolation of nucleic acids.

Figure 6A:
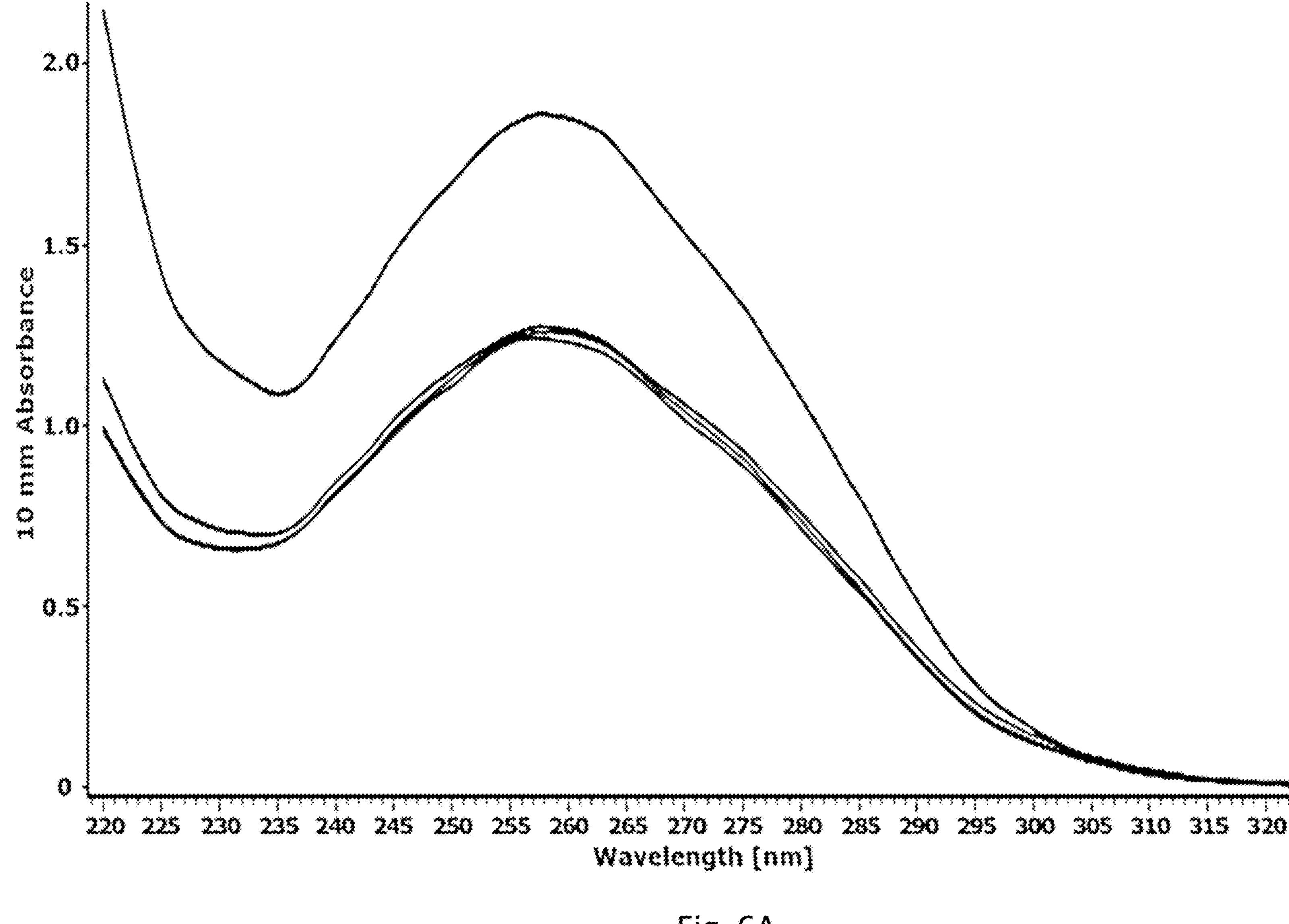
Figure 6B:
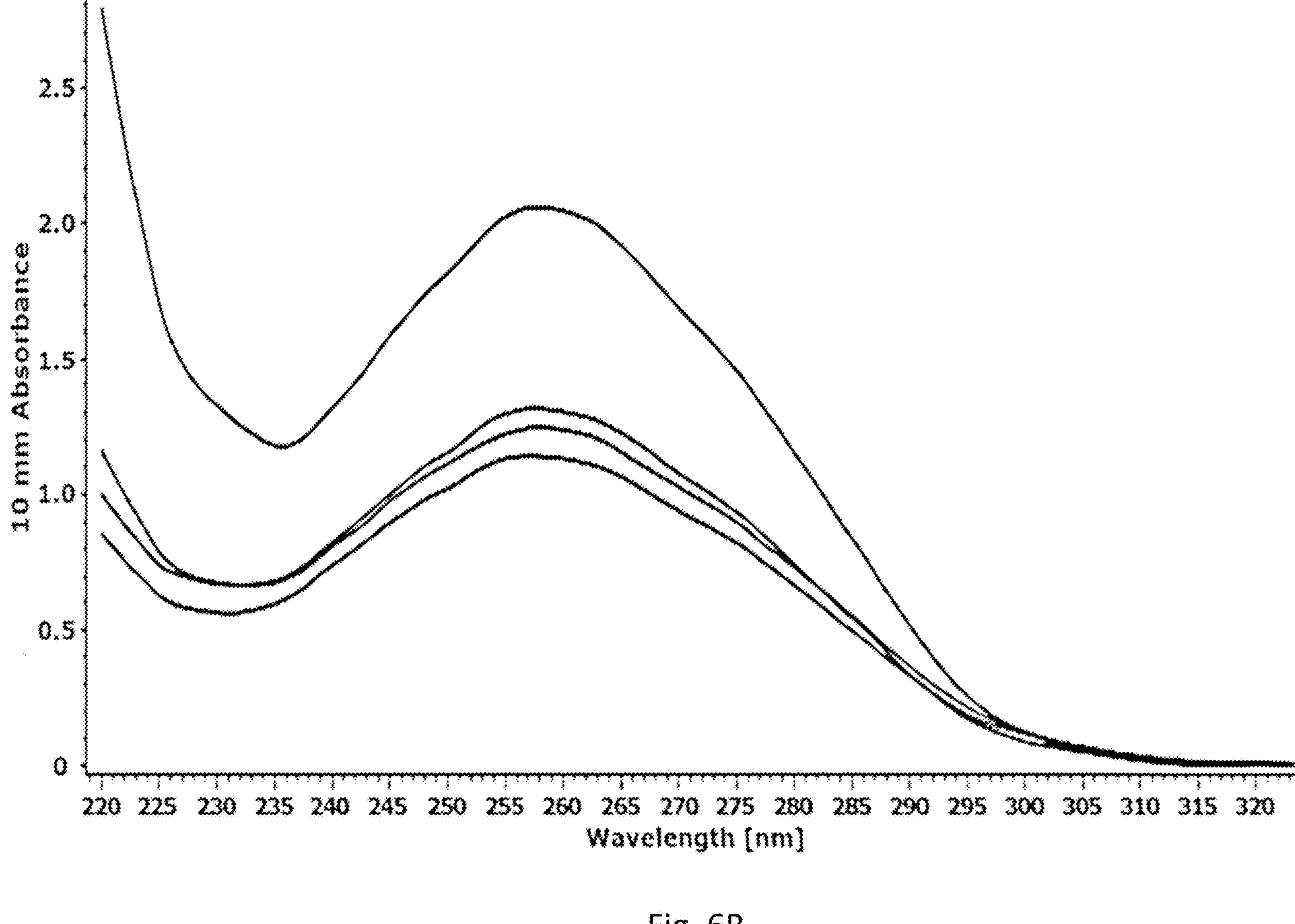
Figure 6C:
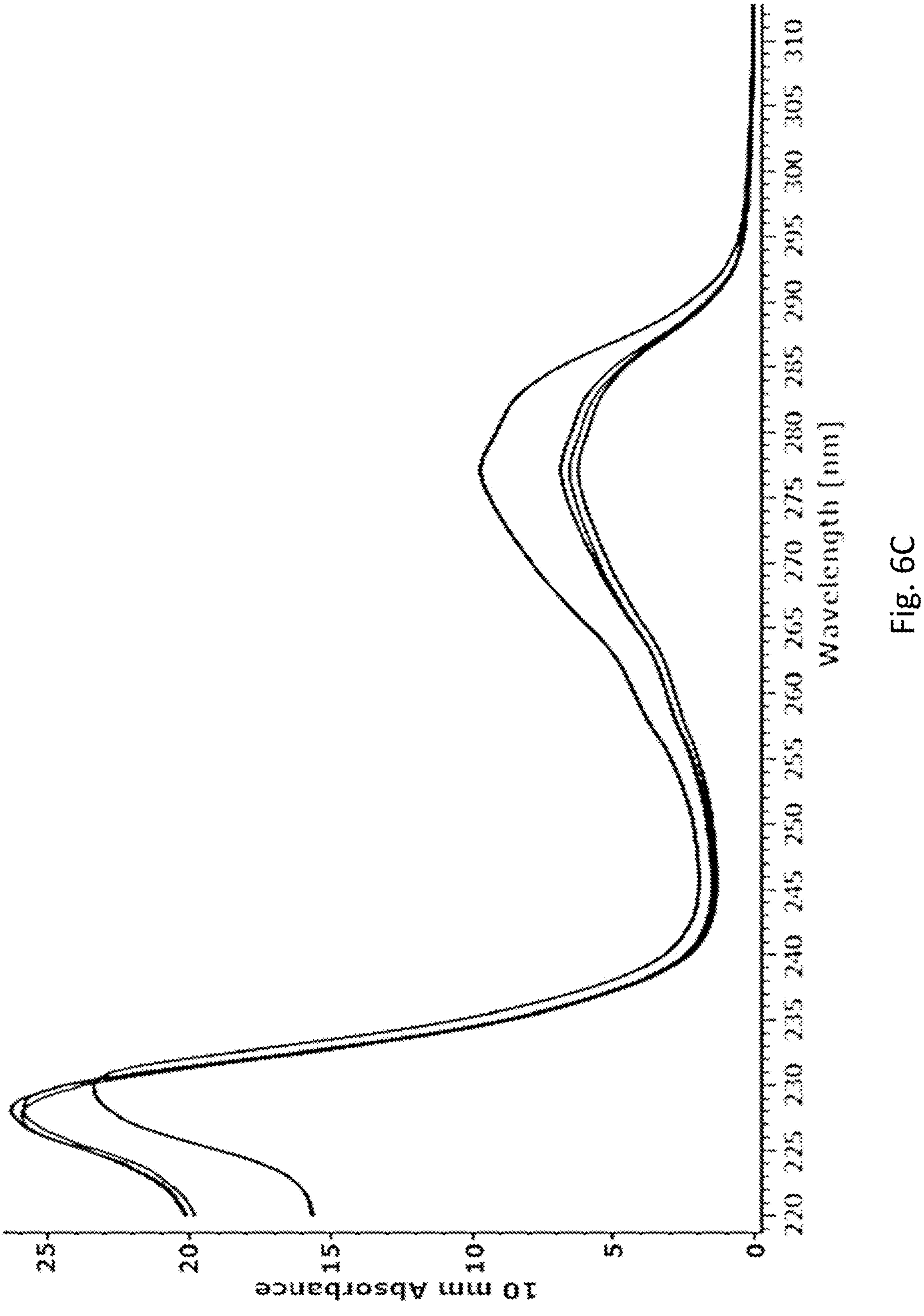
Figure 7:
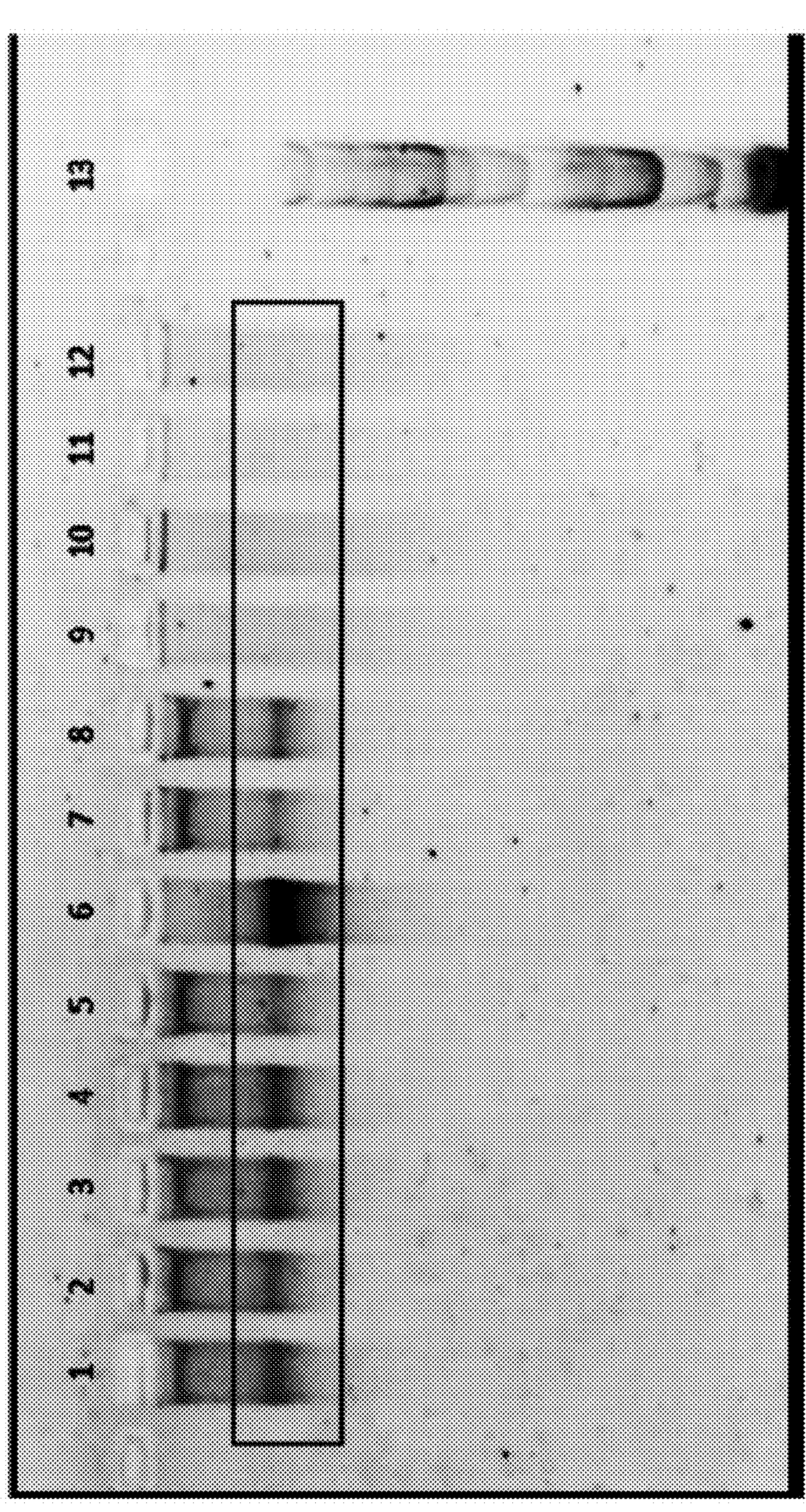

For samples 1-4, the respective photometric measurement is shown in FIG. 6A. For samples 5-8, the respective photometric measurement is shown in FIG. 6B. For samples 9-12, the respective photometric measurement is shown in FIG. 6C.

Gel Electrophoresis:

The respective gel electrophoresis revealed that samples 1-8 showed a strong band of genomic DNA (marked in red), indicating a successful DNA isolation out of the human blood using anionic detergents (SDS and LiDS). In contrast, samples 9-12 showed no band of genomic DNA at all (also marked in red), indicating only an extremely weak or missing DNA isolation.

Therefore, the results indicate that a lysis buffer comprising Triton X-100 as a detergent is not suitable for the isolation of nucleic acids out of human blood.

Summary of Example 14

Both experiments of Example 14 (nucleic acid isolation of gram negative bacteria and human blood) clearly show that Triton X-100 (non-ionic detergent) together with TCEP is unsuitable for a satisfactory lysis. The results reveal a low lysis efficiency for the lysis buffer with Triton X-100, which leads to a strong loss of sensitivity and yield. Furthermore, when Triton X-100 is used, the eluates are highly contaminated, which can have fatal consequences for subsequent applications such as sequencing, PCR, ligation, restriction or other biochemical applications. Absolute photometric quantification is also not possible due to Triton X-100 contamination, which is also very disadvantageous for downstream applications.

Example 15: Protocol for Isolation of Nucleic Acids

Materials Used:

Lysis Buffer Composition:

- 70 mM Sodium—Dodecylsulfate (SDS),
- 50 mM TCEP,
- 0.1 mM EDTA,
- 25 mM TRIS, and
- 50 mM Ammoniumchlorid,
- pH=7.5 (adjusted with NaOH)

Clearing Solution:

2 M $SrCl_2$, and 20 mM TRIS, adjusted with 20.165 ml/L 15% HCl.

Protocol:

1 ml of a culture of *Escherichia coli* was centrifuged at 5000×g for 3 minutes and the supernatant was discarded. The pellet was then resuspended in 100 μL lysis buffer and incubated at 80° C. for 3 minutes. After incubation, 15 μL of clearing solution was added.

Then, the samples were centrifuged at 20000×g, and 100 μL of the supernatant was passed over a column. The column included a filter. made of resin Sephacryl S400. The supernatant was processed through the column by centrifuging for 1 minute at 1000× g.

The resulting eluate contained the isolated DNA/RNA and could readly be used for subsequent downstream applications.

LIST OF REFERENCES

Burden (2008) "Guide to the Homogenization of Biological Samples" Random Primers, Issue No. 7, September 2008, Page 1-14

The invention claimed is:

1. In vitro method for isolating nucleic acids from a sample, the method comprising contacting the sample with a solution, which comprises (a) a buffering substance;

(b) a reducing agent according to formula (I)

(I)

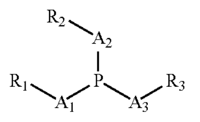

wherein $R_1$, $R_2$ and $R_3$ are independently selected from the group consisting of —H, —$OR_4$, —$COOR_5$, —$P(O)(OR_6)OR_7$, —$N(R_8)R_9$, —$S(O)_{0-2}R_{10}$, and —$SO_3H$;

$R_4$ to $R_{10}$ are independently selected from the group consisting of

—H, and —$(C_1$-$C_{15})$alkyl;

$A_1$, $A_2$ and $A_3$ are independently selected from the group consisting of

—$(C_1$-$C_{15})$alkylene-, —$(C_3$-$C_{10})$cycloalkylene-, —$(C_2$-$C_{15})$alkenylene-;

$A_1$, $A_2$ and $A_3$ optionally are further substituted with one or more substituents selected from —$OR_4$, —$COOR_5$, and —$(C_1$-$C_{15})$alkyl;

and a salt thereof, and (c) an anionic detergent, wherein the anionic detergent is sodium dodecyl sulfate (SDS) or lithium dodecyl sulfate (LiDS); and wherein the method does not include a step of contacting the sample with an enzyme, and wherein the method further comprises the step of contacting the sample with a clearing solution, wherein the clearing solution comprises a cationic ion, and wherein the cationic ion is $K^+$, $Rb^+$, $Cs^+$, $Mg^{++}$, $Ca^{++}$, $Sr^{++}$ or $Ba^{++}$, and wherein the method further comprises a step of separating non-nucleic acid components from the nucleic acids comprising the transfer of the sample, after contacting the sample with the clearing solution, onto a matrix capable of retaining non-nucleic acid components, while the nucleic acids pass through the matrix, and wherein the matrix is a gel filtration matrix.

2. The method of claim 1, wherein the nucleic acids remain in solution during all method steps.

3. The method of claim 1, wherein the isolated nucleic acids are analyzed by PCR, next generation sequencing, SNP genotyping or RT-PCR.

4. The method of claim 1, wherein i) $R_1$, $R_2$ and $R_3$ are independently selected from the group consisting of —H, —$OR_4$, —$COOR_5$, —$P(O)(OR_6)OR_7$, —$S(O)_{0-2}R_{10}$, and —$SO_3H$, optionally from —H, —OH, and —COOH, and ii) $R_4$ to $R_{10}$ are —H, and iii) $A_1$, $A_2$ and $A_3$, are independently selected from the group consisting of —$(C_1$-$C_9)$alkylene-, —$(C_3$-$C_9)$cycloalkylene-, —$(C_2$-$C_9)$alkenylene-;

optionally —$(C_1$-$C_5)$alkylene-, —$(C_3$-$C_6)$cycloalkylene-, —$(C_2$-$C_5)$alkenylene-, and iv) $A_1$, $A_2$ and $A_3$, are independently selected from the group consisting of —(C1-C9)alkylene- and —$(C_2$-$C_9)$alkenylene-, optionally —$(C_1$-$C_5)$alkylene-, and —$(C_2$-$C_5)$alkenylene-, optionally —$(C_1$-$C_3)$alkylene-, and —$(C_2$-$C_3)$alkenylene-, and v) $A_1$, $A_2$ and $A_3$ optionally are further substituted with one or more substituents selected from —$OR_4$ or —$(C_1$-$C_{15})$alkyl.

5. The method of claim 1, wherein the solution further comprises a complexing agent.

6. The method of claim 1, wherein the isolating of nucleic acids from a sample is at a temperature of at least about 40° C., 60° C. or 80° C. for at least 10 seconds.

7. The method of claim 1, wherein the anionic detergent is sodium dodecyl sulfate (SDS).

8. The method of claim 1, wherein the reducing agent is tris(2-carboxyethyl)phosphine (TCEP).

9. The method of claim 1, wherein the reducing agent is tris(2-carboxyethyl)phosphine (TCEP) and the anionic detergent is sodium dodecyl sulfate (SDS).

10. The method of claim 1, wherein the buffering substance is TRIS or TRIS-HCl.

11. The method of claim 1, wherein the buffering substance is TRIS or TRIS-HCl, the reducing agent is tris(2-carboxyethyl)phosphine (TCEP) and the anionic detergent is sodium dodecyl sulfate (SDS).

12. The method of claim 1, wherein the cationic ion is $Mg^{++}$, $Ca^{++}$, $Sr^{++}$ or $Ba^{++}$.

13. The method of claim 9, wherein the clearing solution is $SrCl_2$.

14. The method of claim 1, wherein the reducing agent is present in the solution in a concentration from about 20 mM to 100 mM.

15. The method of claim 8, wherein the reducing agent is present in the solution in a concentration from about 20 mM to 100 mM.

16. The method of claim 1, wherein the clearing solution comprises about 1 M to about 2 M $SrCl_2$.

17. The method of claim 1, wherein the reducing agent is selected from the group consisting of Tris(2-carboxyethyl) phosphine (TCEP), Tris(hydroxymethyl)phosphine, Tris(hydroxymethyl)phosphine, and Tris(hydroxypropyl)phosphine.

* * * * *